US006743640B2

(12) United States Patent
Whitten et al.

(10) Patent No.: US 6,743,640 B2
(45) Date of Patent: Jun. 1, 2004

(54) FLUORESCENT POLYMER-QTL APPROACH TO BIOSENSING

(75) Inventors: David G. Whitten, Santa Fe, NM (US); Duncan W. McBranch, Santa Fe, NM (US); Robert Jones, Albuquerque, NM (US); Troy S. Bergstedt, Cochiti Lake, NM (US)

(73) Assignee: QTL Biosystems LLC, Santa Fe, NM (US)

( * ) Notice: Subject to any disclaimer, the term of this patent is extended or adjusted under 35 U.S.C. 154(b) by 1 day.

(21) Appl. No.: 09/850,074

(22) Filed: May 8, 2001

(65) Prior Publication Data

US 2002/0051985 A1 May 2, 2002

Related U.S. Application Data

(60) Provisional application No. 60/202,647, filed on May 8, 2000, and provisional application No. 60/226,902, filed on Aug. 23, 2000.

(51) Int. Cl.[7] .............................................. G01N 33/543

(52) U.S. Cl. ....................... 436/518; 435/7.1; 435/7.92; 436/164; 436/808; 536/24.31

(58) Field of Search ........................ 435/5, 6, 7.1, 7.92, 435/968; 436/501, 504, 518, 808, 536, 164; 536/23.1, 24.31, 24.32; 530/300, 350

(56) References Cited

U.S. PATENT DOCUMENTS

| | | | | |
|---|---|---|---|---|
| 4,948,843 A | | 8/1990 | Roberts et al. | |
| 4,950,587 A | | 8/1990 | Roberts et al. | |
| 5,194,393 A | * | 3/1993 | Hugl et al. | 436/525 |
| 5,420,016 A | * | 5/1995 | Boguslaski et al. | 435/12 |
| 5,612,221 A | | 3/1997 | Simons et al. | |
| 5,777,096 A | * | 7/1998 | Grossman et al. | 536/24.3 |
| 5,968,762 A | | 10/1999 | Jadamec et al. | |

FOREIGN PATENT DOCUMENTS

| | | |
|---|---|---|
| WO | 99/35288 | 7/1999 |
| WO | 00/66790 | 11/2000 |

OTHER PUBLICATIONS

Decher, "Fuzzy Nanoassemblies: Toward Layered Polymeric Multicomposites", Science, vol. 277, pp. 1232–1237 (1997).

Gallot, et al., "Poly(L–lysine) containing azobenzene units in the side chains: influence of the degree of substitution on liquid crystalline structure and thermotropic behaviour", Liquids Crystals, vol. 23, No. 1, pp. 137–146 (1997).

Place, et al., "Stabilization of the Aggregation of Cyanine Dyes at the Molecular and Nanoscopic Level", Langmuir, vol. 16, No. 23, pp. 9042–9048 (2000).

Jones, et al., "Superquenching and Its Applications in J–Aggregated Cyanine Polymers", Langmuir, vol. 17, No. 9, pp. 2568–2571 (2001).

Decher, et al., "Buildup of Ultrathin Multilayer Films by a Self–Assembly Process: II. Consecutive Adsorption of Anionic and Cationic Bipolar Amphiphiles and Polyelectrolytes on Charged Surfaces", Ber. Bunsenges Phys. Chem., vol. 95, No. 11, pp. 1430–1434 (1991).

Melpolder, et al., "Dye–Polymer/Sol–Gel Composites", Advanced Composite Materials, pp. 287–293 (1994).

Suarez–Rodriguez, et al., "Flavanol fluorescent flow–through sensing based on a molecular imprinted polymer", Analytica Chimica Acta., vol. 405, pp. 67–76 (Jan. 2000).

Rathbone, et al., "Molecular recognition by fluorescent imprinted polymers", Tetrahedron Letters, vol. 41, pp. 123–126 (Jan. 2000).

Chen, et al., "Highly sensitive biological and chemical sensors based on reversible fluorescence quenching in a conjugated polymer", PNAS, vol. 96, No. 22, pp. 12287–12292 (Oct. 1999).

* cited by examiner

*Primary Examiner*—Long V. Le
*Assistant Examiner*—Gary W. Counts
(74) *Attorney, Agent, or Firm*—Piper Rudnick LLP; Steven B. Kelber

(57) ABSTRACT

A chemical composition including a moiety comprising a quencher (Q), a tethering element (T), and a ligand (L) that associates with and quenches a fluorescent polymer is disclosed. When an analyte sample is introduced, the ligand (L) binds to a target biological agent if it is present, thereby causing the QTL molecule to separate from the fluorescent polymer resulting in an increase in detected fluorescence. The same chemistry is advantageously employed in a competitive assay. An electric field can also be applied to separate the QTL molecule from the fluorescent polymer. A method for detecting targets for these methods are also disclosed.

18 Claims, 20 Drawing Sheets

1

2

3

4

5

6

7

FLUORESCENT POLYMER-QTL APPROACH TO BIOSENSING

This application claims priority from U.S. Provisional Application Serial No. 60/202,647 filed May 8, 2000 and U.S. Provisional Application Serial No. 60/226,902 filed Aug. 23, 2000. The entirety of those provisional applications are incorporated herein by reference.

BACKGROUND OF THE INVENTION

Field of the Invention

The present invention relates to a fluorescent biosensor that functions by a novel Quencher-Tether-Ligand (QTL) mechanism. In particular, the polymer-QTL system provides for effective sensing of biological agents by observing fluorescence changes.

DISCUSSION OF THE BACKGROUND

The enzyme linked immunosorbant assay, ELISA, is the most widely used and accepted technique for identifying the presence and biological activity of a wide range of proteins, antibodies, cells, viruses, etc. It is a multi-step "sandwich assay" in which the analyte biomolecule is first bound to an antibody tethered to a surface. A second antibody then binds to the biomolecule. In some cases, the second antibody is tethered to a catalytic enzyme which subsequently "develops" an amplifying reaction. In other cases, this second antibody is biotinylated to bind a third protein (e.g., avidin or streptavidin). This protein is tethered either to an enzyme, which creates a chemical cascade for an amplified colorimetric change, or to a fluorophore, for fluorescent tagging.

Despite its wide use, there are many disadvantages to ELISA. For example, because the multi-step procedure requires both precise control over reagents and development time, it is time-consuming and prone to "false positives". Further, careful washing is required to remove nonspecific adsorbed reagents. On the other hand, the polymer-QTL (Quencher-Tether-Ligand) approach of the present invention is a single-step, instantaneous, homogeneous assay where the amplification step is intrinsic to the fluorescent conjugated polymer. Furthermore, there are no reagents. Thus, the process is uniquely robust, simple, and accurate relative to ELISA or other sensor techniques.

Other technology advantages inherent in the polymer-QTL approach are similar to those used in fluorescence resonance energy transfer (FRET). FRET techniques have been applied to both polymerase chain reaction-based (PCT) gene sequencing and immunoassays. In particular, FRET uses homogeneous binding of an analyte biomolecule to activate the fluorescence of a dye that is quenched in the off-state. However, there are important limitations and differentiations to FRET relative to the polymer-QTL approach. In an example of FRET technology, a fluorescent dye is linked to an antibody (F-Ab), and this diad is bound to an antigen linked to a quencher (Ag-Q). The bound complex (F-Ab:Ag-Q) is quenched (i.e., non-fluorescent) by energy transfer. In the presence of identical analyte antigens which are untethered to Q (Ag), the Ag-Q diads are displaced quantitatively as determined by the equilibrium binding probability determined by the relative concentrations, [Ag-Q]/[Ag]. This limits the FRET technique to a quantitative assay where the antigen is already well-characterized, and the chemistry to link the antigen to Q must be worked out for each new case.

On the other hand, the QTL assay works by selective binding to the quencher-tether-ligand. The competition between the binding of QTL to the polymer vs. the analyte may be widely controlled by varying the polymer and QTL structure and charge density. Even more importantly, the QTL assay uses a fluorescent polymer rather than a small molecular fluorophore. This fundamental difference between FRET techniques and QTL assays allows the polymer-QTL technology to have significant amplification in quenching and detection sensitivity. In addition, the polymer-QTL approach is immediately applicable to powerful combinatorial techniques for generating new molecular recognition species for unknown and uncharacterized biomolecules. Due to the sensitivity of fluorescence quenching in the QTL technology relative to FRET, QTL eliminates the need for pre-concentration of the sample, thereby allowing the use of microliter quantities of reagents in capillary tubes. The polymer-QTL approach also avoids the elaborate preprocessing required by polymerase chain reaction (PCR), offering significant incentives to the further development of the polymer-QTL approach for detection of nucleic acids.

The ability to rapidly and accurately detect and quantify biologically relevant molecules with high sensitivity is a central issue for medical technology, national security, public safety, and civilian and military medical diagnostics. Many of the currently used approaches, including enzyme linked immunosorbant assays (ELISAs) and PCR are highly sensitive. However, they can be cumbersome and time-consuming, as discussed above. In order to address the problems in the art, the present inventors have developed a prototype for a new fluorescent biosensor which functions by a novel Quencher-Tether-Ligand (QTL) mechanism that provides a simple, rapid and highly-sensitive detection of biological molecules with structural specificity. The present invention may be adapted to a number of different formats ranging from a single or multiple species to medical diagnostics and fluorescent tags.

SUMMARY OF THE INVENTION

It is an object of the present invention to provide a novel chemical moiety formed of a quencher (Q), a tethering element (T), and a ligand (L).

It is another object of the present invention to provide a method of detecting target biological agents in a sample using the novel QTL molecule of the present invention and a fluorescent polymer.

It is a further object of the present invention to detect target biological agents in a sample by observing fluorescent changes.

It is a feature of the present invention that the change in fluorescence is indicative of the presence of the target biological agent.

It is another feature of the present invention that the fluorescent polymer can be tethered to the novel QTL molecule.

It is a further feature of the present invention that the fluorescent polymer used in detection can be anchored to a support.

It is an object of the present invention to rapidly and accurately detect and quantify target biological molecules in a sample.

It is a further feature of the invention that the fluorescent polymer comprises dye chromophores pendant as side chains of a polymeric backbone.

It is an advantage of the present invention that target biological molecules can be detected at near single molecule levels.

It is a further feature of the invention that detection of target molecules may be enhanced by application of electric fields.

It is a further advantage of the present invention that it is simple and requires no elaborate preprocessing.

These and other objects are met by a composition of matter comprising: a) a fluorescent polymer, and b) a chemical moiety QTL comprising a recognition element, which binds to a target biological agent, and a property-altering element which alters fluorescence emitted by the fluorescent polymer when complexed together to a distinguishable degree, bound together by a tethering element, the chemical moiety being adapted for complexation with the fluorescent polymer. In the presence of binding of the recognition element to said target biological agent, the fluorescence emitted by the polymer is altered from that emitted when binding between said recognition element and said target biological agent does not occur.

DESCRIPTION OF THE PREFERRED EMBODIMENTS

The key scientific basis for the polymer-QTL approach is the amplification of quenching of fluorescence that can be obtained with certain charged conjugated polymers and small molecule quenchers. One polymer that has been used is a water soluble polyelectrolyte, 2 methoxy-5-(3-sulfonato-propyloxy)-polyphenylene vinylene (MPS-PPV). Its strong fluorescence can be quenched by the addition of extremely low levels of cationic electron acceptors such as methyl viologen ($MV^{2+}$). The fluorescence quenching is measured quantitatively by the Stem-Volmer quenching constant, Ksv (see equation [1] set forth below). In equation [1], $I_0$ is the fluorescence intensity in the absence of Q and I is the intensity at a quencher concentration, [Q].

$$\frac{I_0}{I} = 1 + K_{SV}[Q] \qquad [1]$$

Figure 1:
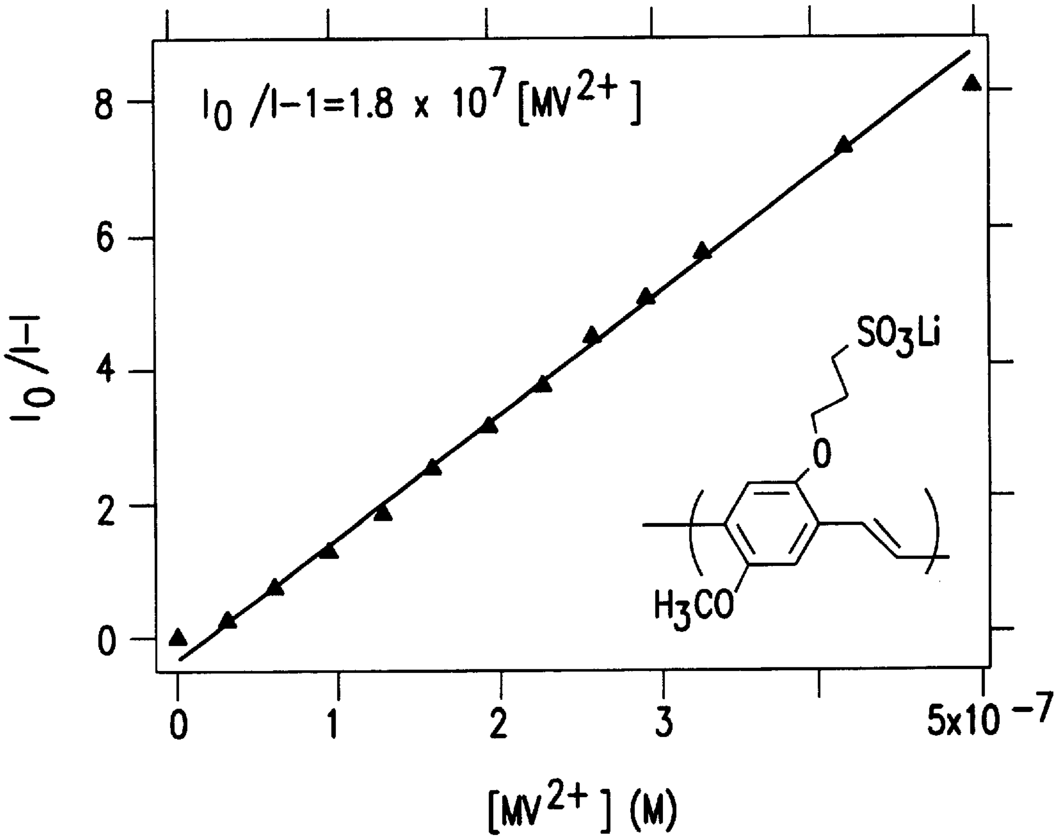
FIG. 1 is a Stern-Volmer plot of fluorescence intensity of the polymer MPS-PPV in the presence of methyl viologen ($MV^{2+}$).

By way of comparison, the quenching constant, $K_{SV}$, observed for $MV^{2+}$ with trans-stilbene, the molecular repeat unit of MPS-PPV, is 15 while that for the polymer MPS-PPV is $1.8\times10^7$ (see FIG. 1). Chen et al., Proc. Natl. Acad. Sci., 1999:96, 12287–12292. The more than million-fold enhancement of sensitivity to quenching indicates that the complexation of a single quencher molecule to a single site on the polymer chain can quench the fluorescence of the entire polymer chain. In the polymer-QTL approach, the quencher forms a relatively weak complex with the polymer, and the formation of the large and tight complex between the bioagent and the ligand results in a pulling away of the quencher from the polymer and reversal of the fluorescence quenching.

Figure 2:
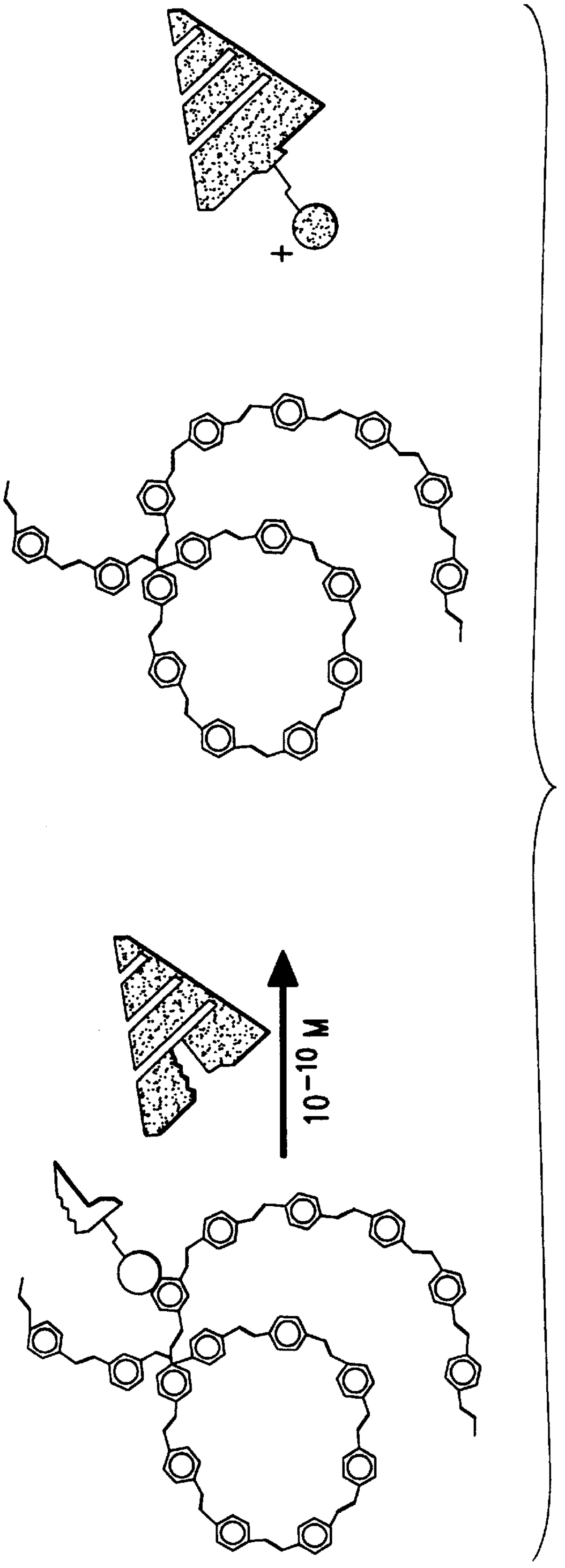
FIG. 2 is a general illustration of the mechanism of the present invention.

This concept is illustrated schematically in FIG. 2, using the protein avidin as the receptor. It was determined that the QTL molecule quenches nearly as well as $MV^{2+}$ and can be used over a wide dynamic range. The QTL molecule shown in FIG. 2 is not removed by other proteins and a quencher that does not contain biotin is not removed by the addition of avidin. The QTL concept is not limited to biotin/avidin combination, it works for other ligand/receptor combinations (e.g., GM1/Choleratoxin, antibody/antigen, and hormone/receptor). Additionally, in the polymer-QTL approach, the identification of the ligand is highly specific to the desired analyte receptor. Thus, the recognition of the analyte receptor can take place at sub-nanomolar levels of the receptor. This specificity of the receptor for the desired analyte results in a highly sensitive mechanism for detecting the desired analyte.

In the polymer-QTL approach, the sensitivity is defined by three parameters. The first parameter to be determined is the value of Ksv. For systems employing the polymer-QTL approach, Ksv is approximately $10^7$–$10^9$ $M^{-1}$ for a polymer concentration of $10^{-9}$ M. The second parameter, the level of minimal detectable variation of I (i.e., $\Delta I/I$) must then be determined. Using modulation of the light sources and lock-in detection, it is reasonable to assume a $\Delta I/I$ of an order of $10^{-3}$. The third parameter, the number of receptor sites, $N_R$, on the biomolecule of interest can be calculated, since the concentration of quencher removed is given by the equation $[Q]=N_R[B]$, where [B] is the concentration of the biomolecule to be detected. For example, for a biotin/avidin system, $N_R=4$. On the other hand, $N_R$ is higher for the GM1/Choleratoxin system. Therefore, biomolecules with large numbers of binding sites have additional amplification of sensitivity. Using these simple relations, the trade-off between sensitivity and dynamic range may be estimated as follows.

First, an expression for the minimum detectable concentration of biomolecule, $[\Delta B](=[\Delta Q]/N_R)$ can be derived from equation [1]:

$$[\Delta B]=[\Delta I/I](1+K_{SV}[Q])/(K_{SV}*N_R) \qquad [2]$$

Figure 3A:
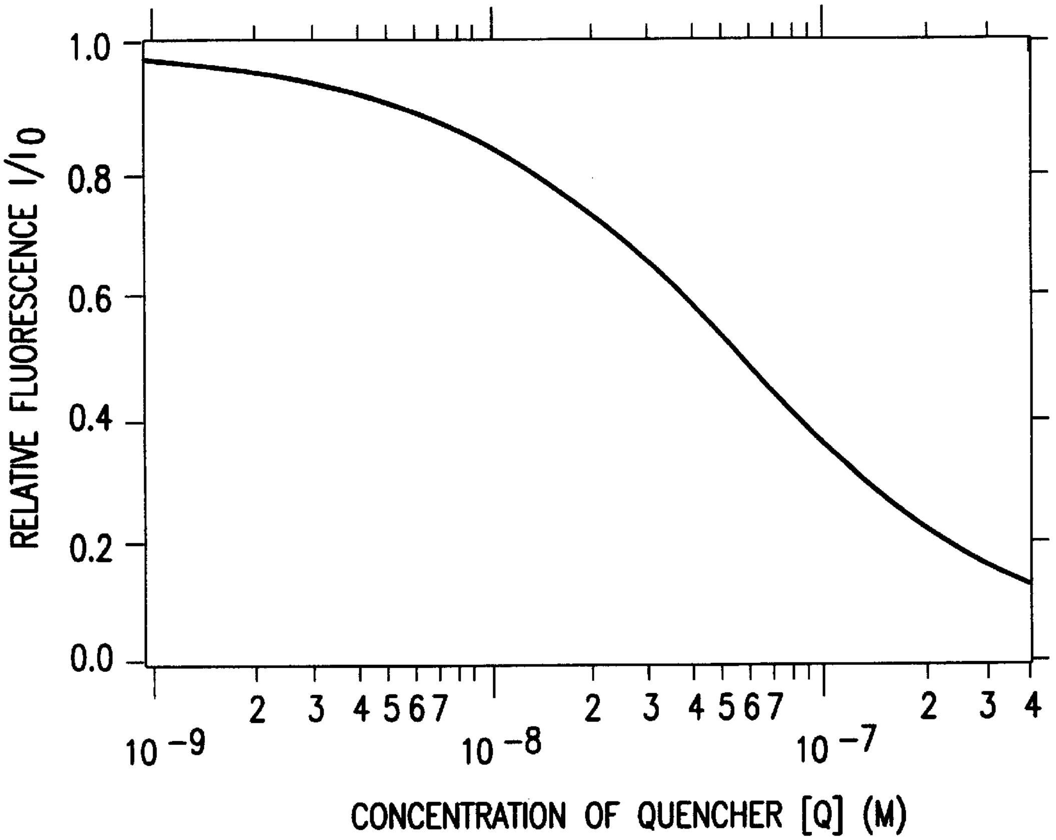
FIG. 3*a* is a graphical illustration of the relative fluorescence intensity for a sensor based on Stern-Volmer type quenching and recovery.
Figure 3B:
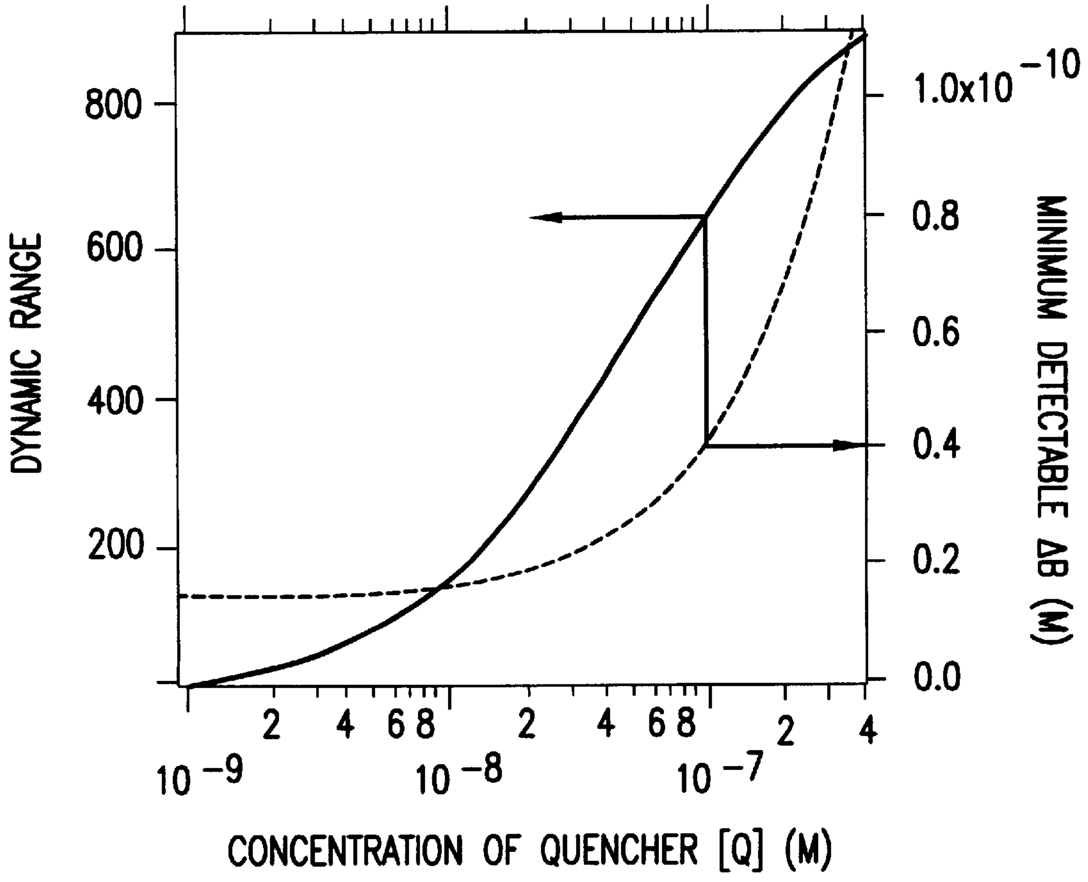
FIG. 3*b* is a graphical illustration of the sensitivity and dynamic range for a sensor based on Stern-Volmer type quenching and recovery.

Next, the maximum detectable concentration of biomolecule, [B] (i.e., the concentration of B which removes all of the available QTL molecules), is calculated from the equation $[B]=[Q]/N_R$. These expressions are illustrated in FIGS. 3*a* and 3*b*, which show the fluorescence intensity (FIG. 3*a*) and dynamic range and sensitivity (FIG. 3*b*) as a function of the QTL molecule. From FIGS. 3*a* and 3*b*, it can be seen that increasing sensitivity is compensated by a decreased dynamic range, and vice versa. However, a compromised value of [Q] can be selected which allows attractive values for both parameters, as illustrated by the arrows in FIG. 3*b*. In FIG. 3*b*, [Q] is approximately $10^{-7}$ M, the dynamic range is 650, and the sensitivity is 40 pM. By having several solutions with varying concentrations of polymer, sequential detection at a much greater dynamic range and over a range of sensitivities variable from those relevant for detecting bioterrorism agents (less than picomolar concentrations) to those relevant for in vitro and in vivo medical diagnostics (nanomolar to micromolar) is possible.

Figure 4:
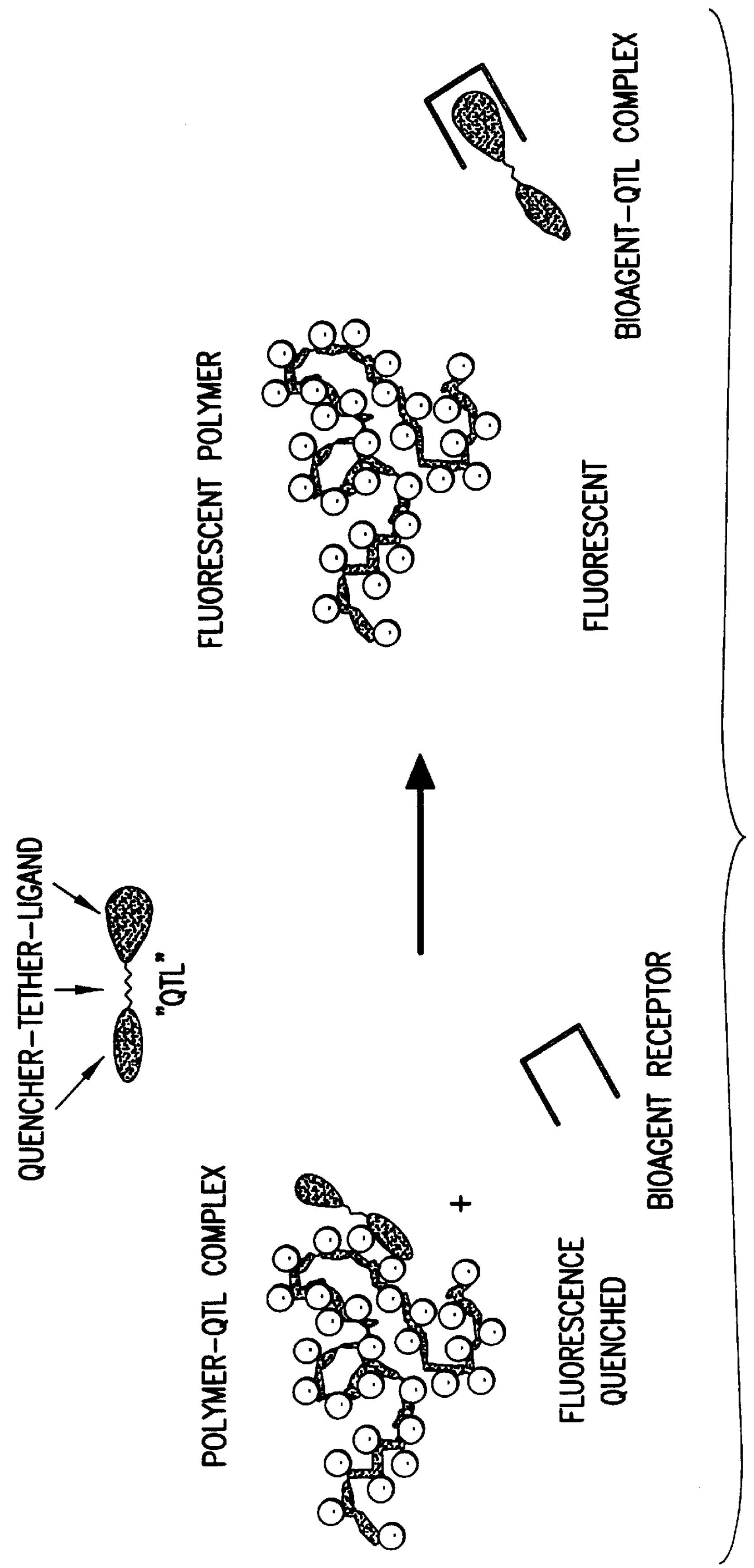
FIG. 4 is a general illustration of the QTL approach.

In the "biosensor" mode, the polymer-QTL approach functions by having a fluorescent polymer quenched by a specially constructed "quencher-tether-ligand" (QTL) unit as shown in the diagram set forth in FIG. 4. Suitable examples of ligands that can be used in the polymer-QTL approach of the present invention include chemical ligands, hormones, antibodies, antibody fragments, oligonucleotides, antigens, polypeptides, glycolipids, proteins, protein fragments, enzymes, peptide nucleic acids and polysaccharides. Examples of quenchers for use in the QTL molecule include methyl viologen, quinones, metal complexes, fluorescent dyes, and electron accepting, electron donating and energy accepting moieties. The tethering element can be, for example, a single bond, a single divalent atom, a divalent chemical moiety, and a multivalent chemical moiety. However, these examples of the ligands, tethering elements, and quenchers that form the QTL molecule are not to be construed as limiting, as other suitable examples would be easily determined by one of skill in the art.

The addition of an analyte containing a biological agent specific to the ligand removes the QTL molecule from the fluorescent polymer, which results in a "turning on" of the polymer fluorescence. This technique analyzes the level or presence of the bioagent that is to be detected. Examples of bioagents include proteins, polypeptides, nucleic acids, hormones such as insulin, testosterone, estradiol, drugs such as theophylline, chemical agents such as caffeine, viruses, bacteria such as *E. coli*, microorganisms such as anthrax, antibodies, antibody fragments, and toxins such as choleratoxin, botulinum, and Shigella.

Competitive Assay for Polymer-QTL

Figure 5:
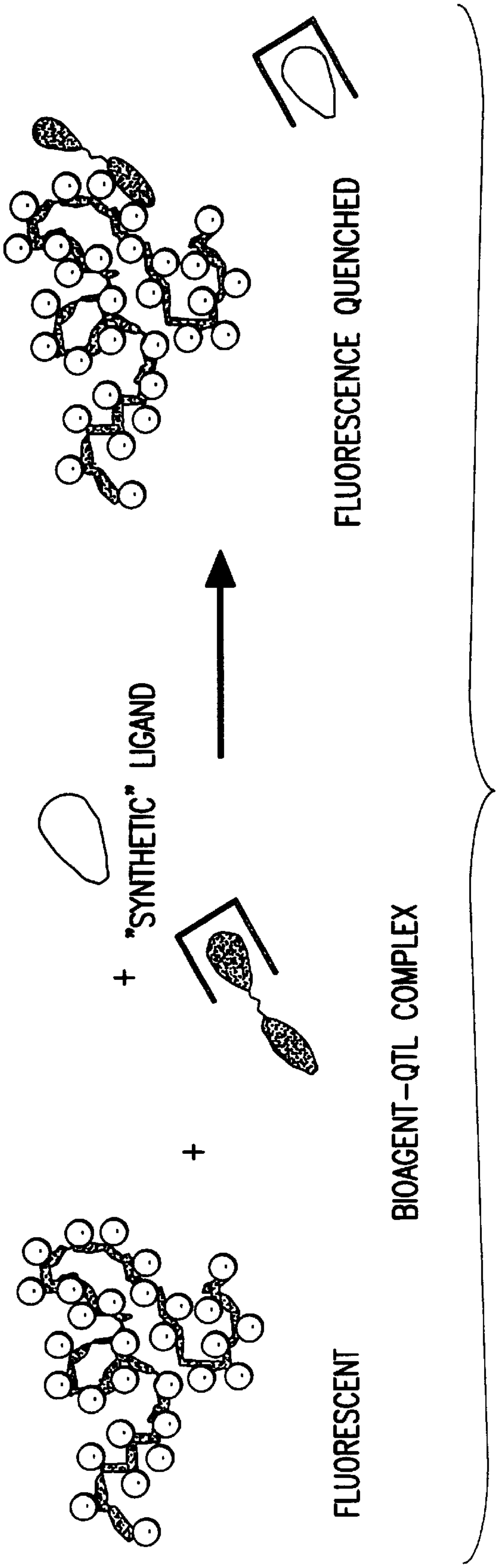
FIG. 5 is a general illustration of an alternative QTL approach.

For screening small-to-moderate sized molecules that may compete with the natural ligand for a particular bioagent, an attractive alternative is to reverse the process shown in FIG. 4. In this case, the QTL molecule is precomplexed with the bioagent and the polymer fluorescence is initially unquenched as shown in FIG. 5. Addition of a natural or synthetic ligand results in competition for the binding site of the bioagent, release of the QTL molecule, and quenching of the polymer fluorescence.

In one embodiment, the ligand of the QTL molecule is a molecule that can bind to the estrogen receptor. The usual estrogen receptor ligand, estradiol, does not lend itself easily to forming a QTL molecule since the hydroxyl groups are essential to the binding. This is easily seen in the crystal structure of the estrogen receptor with bound estradiol. However non-natural ligands such as diethylstilbestrol and tamoxifen can readily be tethered to a quencher using reactive sites remote from the hydroxyl groups essential to binding. Thus, for high throughput screening, the QTL:estrogen receptor complex in the presence of the polymer is unquenched. Addition of a ligand that can compete with the QTL molecule releases the QTL molecule and quenches the polymer fluorescence.

In a preferred embodiment, the QTL molecule contains a xanthine derivative (e.g., caffeine, theophylline) or other agents capable of acting as agonists or antagonists) as the ligand and the complexing agent is one of the adenosine receptors or an antibody to the xanthine. The format for analysis of a xanthine derivative includes a fluorescent polymer in the presence of the QTL:adenosine receptor (or antibody) complex. The polymer fluorescence is unquenched due to the complexing with the QTL molecule. The presence of a potential ligand that can compete for the antibody or adenosine receptor can be detected by the quenching of the polymer fluorescence. The quantitative measurement of fluorescence quenching can also be used to monitor the levels of a specific reagent in samples of variable "ligand" concentration.

In anther preferred embodiment, the QTL material comprises insulin-like growth factor (IGF1) or a fragment and the complexing agent is an IGF1 antibody, IGF1 binding protein or IGF1 receptor. This may be used in an assay to monitor levels of growth hormone in a sample.

In addition, polymer-QTL assays according to the present invention can be used to assay levels of cyclic adenosine monophosphate (cAMP) using a quencher tethered to cAMP and a cAMP antibody as the complexing bioagent. With the QTL:cAMP antibody complex and polymer present, the polymer fluorescence is unquenched. However, quenching occurs when the sample is treated with cAMP. The level of quenching provides a quantitative determination of cAMP.

Detection of Chemical and Biological Agents using J-Aggregated CDP Polymer-QTL Combinations The combination of J-aggregate polymer polyelectrolytes and synthetic Quencher-Tether-Ligand (QTL) molecules for fluorescent sensing is a new composition-of-matter for the qualitative and quantitative assay of biological agents.

Figure 6A:
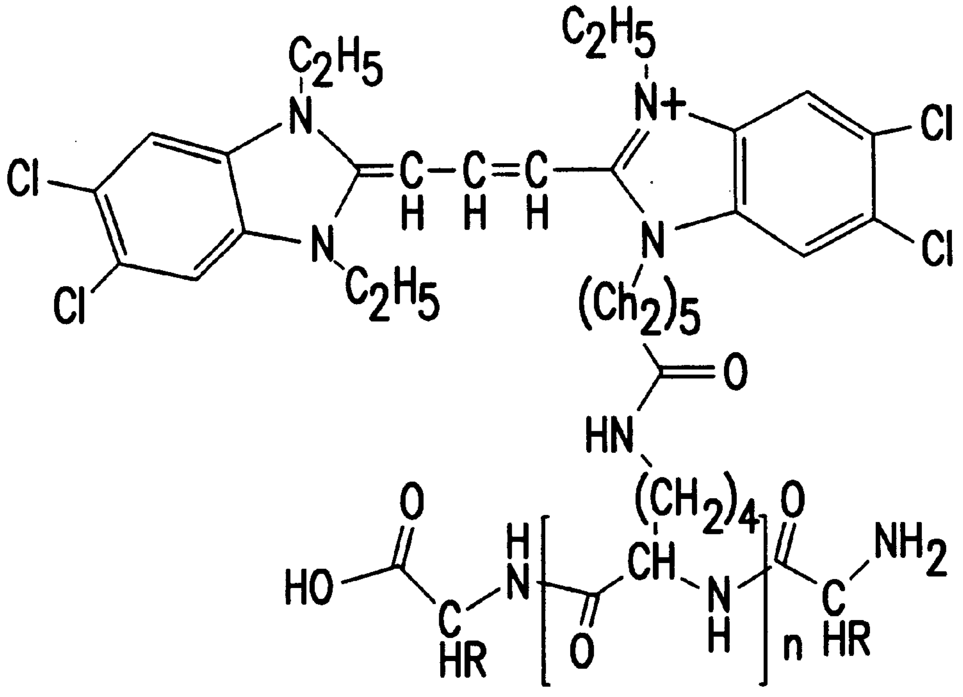
FIG. 6*a* is an illustration of a cyanine dye pendant (CDP) polymer.
Figure 6B:
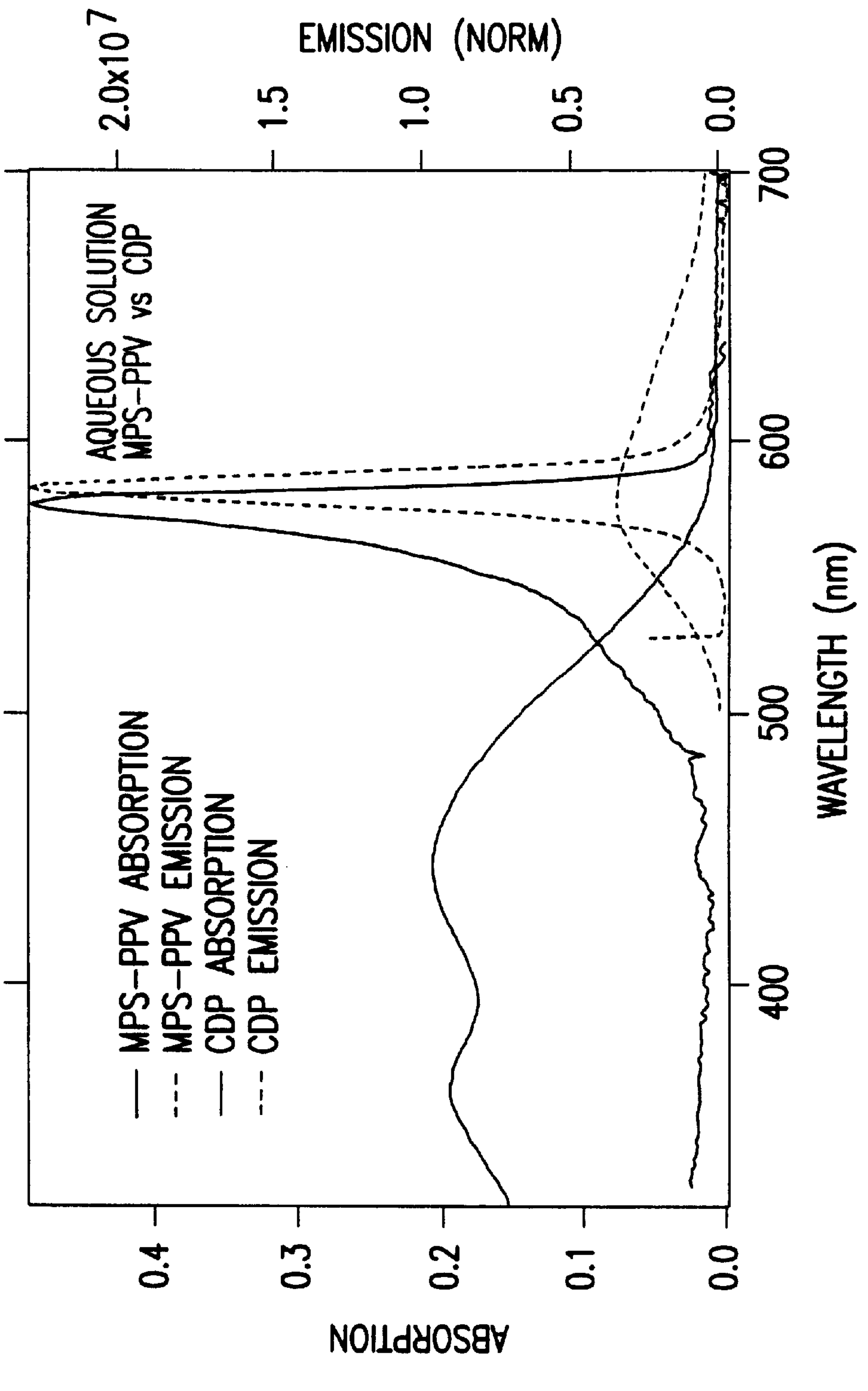
FIG. 6*b* is a graphical illustration of a comparison of J-aggregated CDP and a conjugated polymer absorption and fluorescence spectra.

Dye polymers having an ionic fluorescent dye chromophore on each repeat unit of a non-conjugated polymer have been previously shown to exhibit strong J-aggregate absorption and fluorescence. (See Roberts et al., U.S. Pat. No. 4,950,587, (1990); Roberts et al., Ceramic Trans. (1991), 19:287; and Place et al., Langmuir (2000) 16:9042.) These polymers can exhibit unusually sharp and intense absorption and fluorescence bands, as shown in FIGS. 6*a* and 6*b*. Jones et al., Langmuir, (2001) 17:2568–2571. Further, their polyelectrolyte properties can render them simultaneously water-soluble plastic materials and substances capable of forming thin films when exposed to appropriate surfaces. (See Place et al., Langmuir (2000) 16:9042; and Place et al., unpublished manuscript).

In the polymer-QTL approach of present invention, there is an unprecedented high and unique sensitivity of these formally non-conjugated polymers in both solution and various supported formats to luminescence quenching by certain agents capable of accepting energy or electrons from the photoexcited polymer. The polymer luminescence may also be quenched by electron donor molecules. For example, it has been demonstrated that J-aggregate polymers show "superquenching" sensitivity comparable to or greater than that observed for conjugated polyelectrolytes. Further, the photophysical behavior and properties of these polymers offer significant advantages not recognized in previously disclosed systems.

J-aggregate polymers exhibit readily detectable and characteristic absorption and fluorescence transitions. The narrow and intense fluorescence can easily be detected at polymer concentrations (in repeat units) of $10^{-9}$ M. The sensitivity to "superquenching" of these polymers provides a basis for detection of specific chemicals exhibiting quenching properties at extremely low levels (i.e., chemical sensing).

The narrow absorption and fluorescence bands of these J-aggregated polymers make it possible to follow changes in the luminescence of several different polymers in the same sample (liquid or solid) simultaneously. Since the chromophore does not have to be part of the polymer backbone, it is possible to employ a polymer "scaffold" that possesses independent properties controlling its folding. In one example, poly-1-lysine was used. The protein-mimic "repeat" structure dictates that the polymer will be in one of the common structures observed for folded proteins, for example, an α-helix or a pleated β-sheet. (See Place et al., Langmuir (2000) 16:9042; and Gallot et al., Liquid Crystals (1997), 23:137). There is preliminary evidence suggesting that the dye-derivatized poly-1-lysine exists preferentially in a β-sheet structure. The control of polymer secondary structure by intramolecular hydrogen bonds renders the polymer much less susceptible to influences from reagents such as ions or macromolecules in the medium, and is therefore potentially useful in a broad range of environments and in the presence of diverse reagents which have been shown to perturb both the structure and luminescent properties of previously disclosed conjugated polyelectrolytes.

Each polymer molecule constructed from a poly-amino acid contains an additional functionality at each end of the polymer chain. These functionalities may be used to construct more complex "tailored" biosensor molecules or to attach the polymer to a support, ballast, or bead. Thus, these polymers offer possibilities for constructing a variety of "smart" materials or highly tailored molecular systems for advanced sensing concepts.

Additionally, the construction of a specifically tailored molecule that combines a quencher moiety (Q) with a specific biological ligand or recognition molecule (L) which is linked by a tether (T) (i.e., a QTL molecule) can afford the ability to use these polymers as a platform for the detection of a broad range of biological molecules.

As for previously disclosed fluorescent polyelectrolytes, the QTL molecule having an opposite overall charge to the polyelectrolyte binds weakly and nonspecifically to the polymer by a combination of coulombic and hydrophobic interactions. Quenching at the level of close to one molecule of quencher per polymer chain has been observed. The L portion of the QTL molecule is designed to recognize and bind strongly and specifically to a biological molecule (e.g., protein, nucleic acid, virus, or cell) such that addition of the bioagent to a quenched polymer-QTL results in the removal of the QTL molecule from the polymer and the release of polymer fluorescence. Depending on the nature of the quencher, the bioagent-QTL complex may be non-luminescent or it may emit light at the characteristic luminescence of Q.

Figure 7:
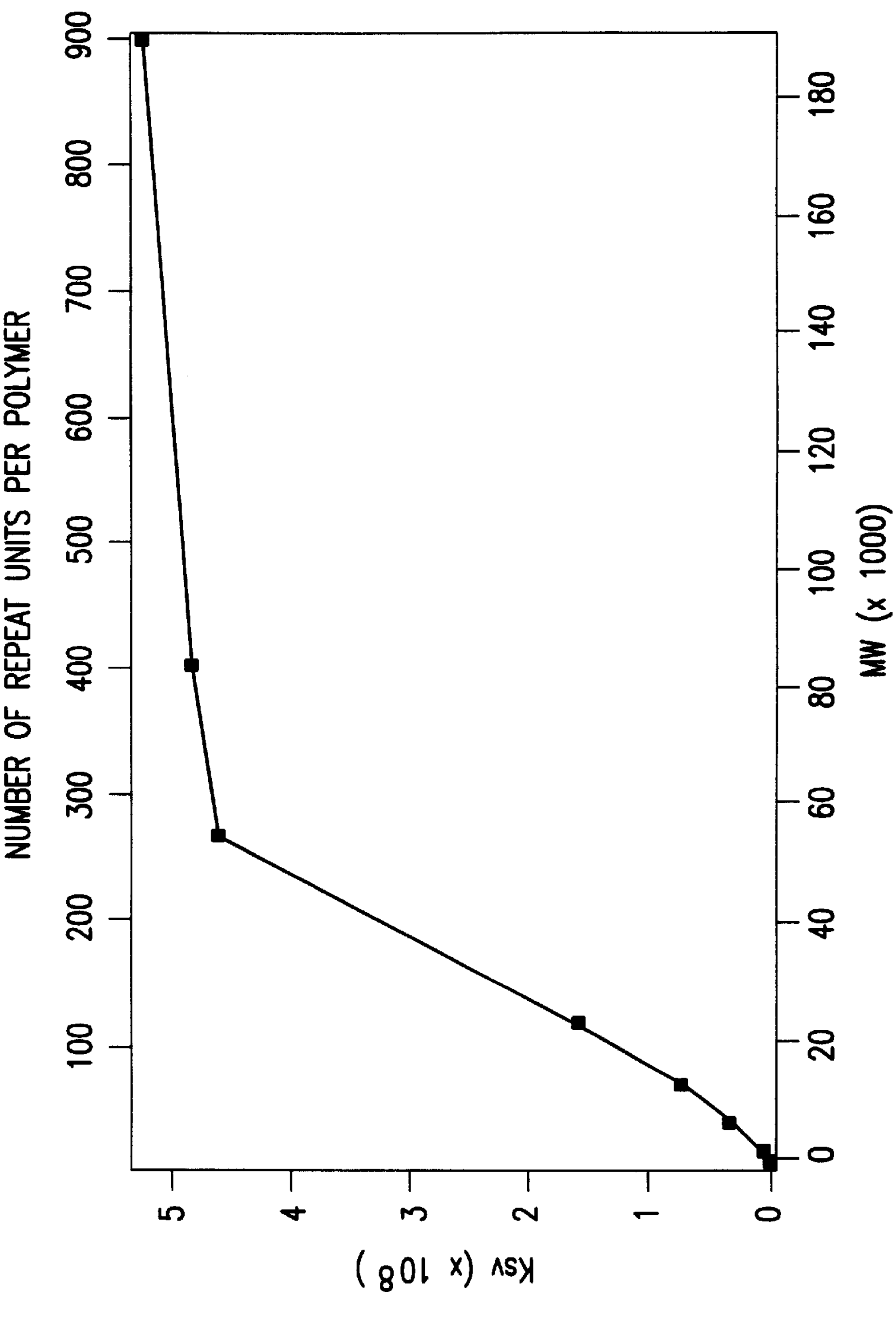
FIG. 7 is a graphical illustration of the variation of the quenching constant, Ksv, for J-aggregate CDP as a function of number of polymer repeat units (PRU).
Figure 8A:
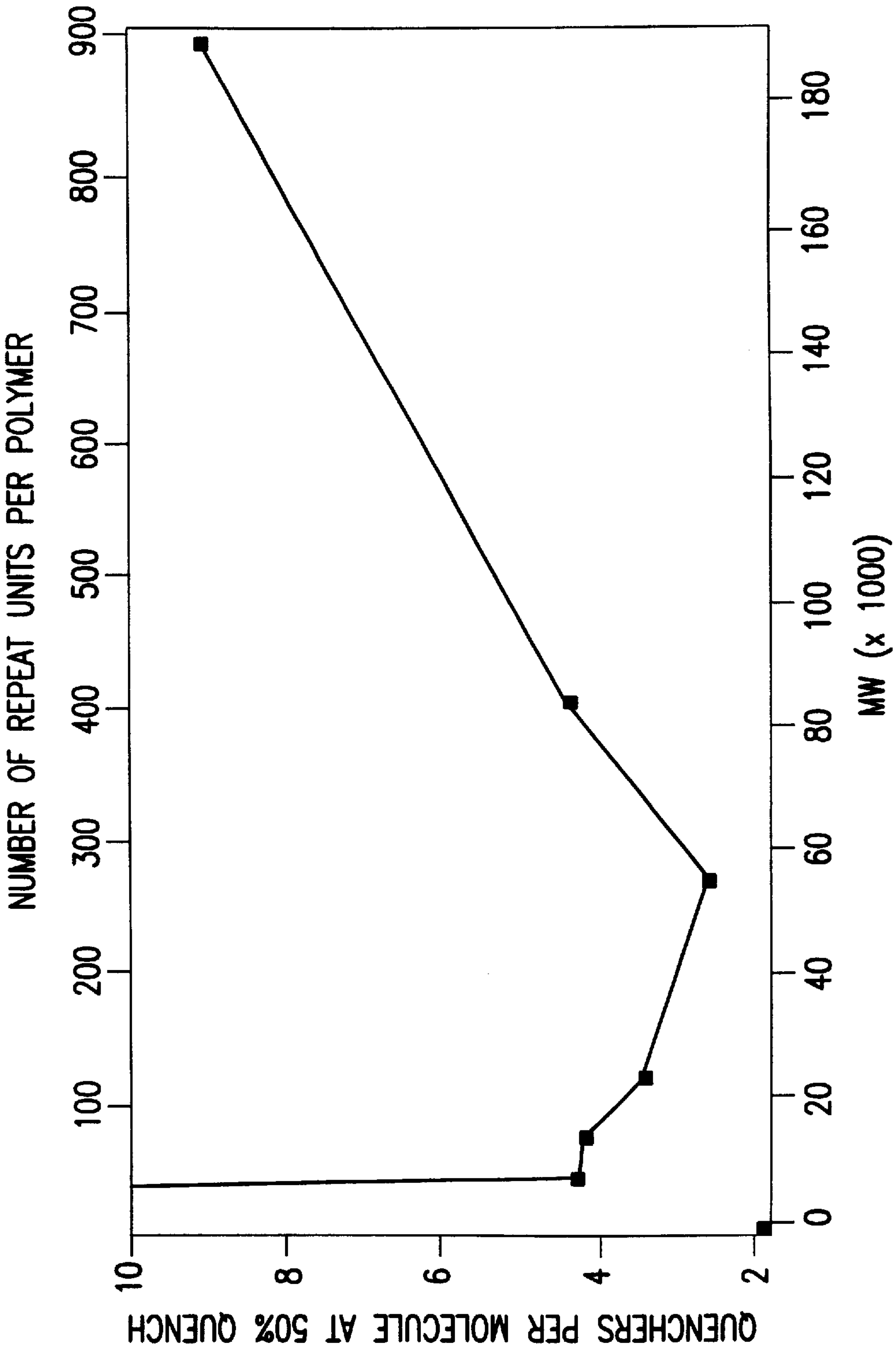
FIG. 8*a* is a graphical illustration of quenchers per polymer at 50% quenching as a function of the number of polymer repeat units (PRU).
Figure 8B:
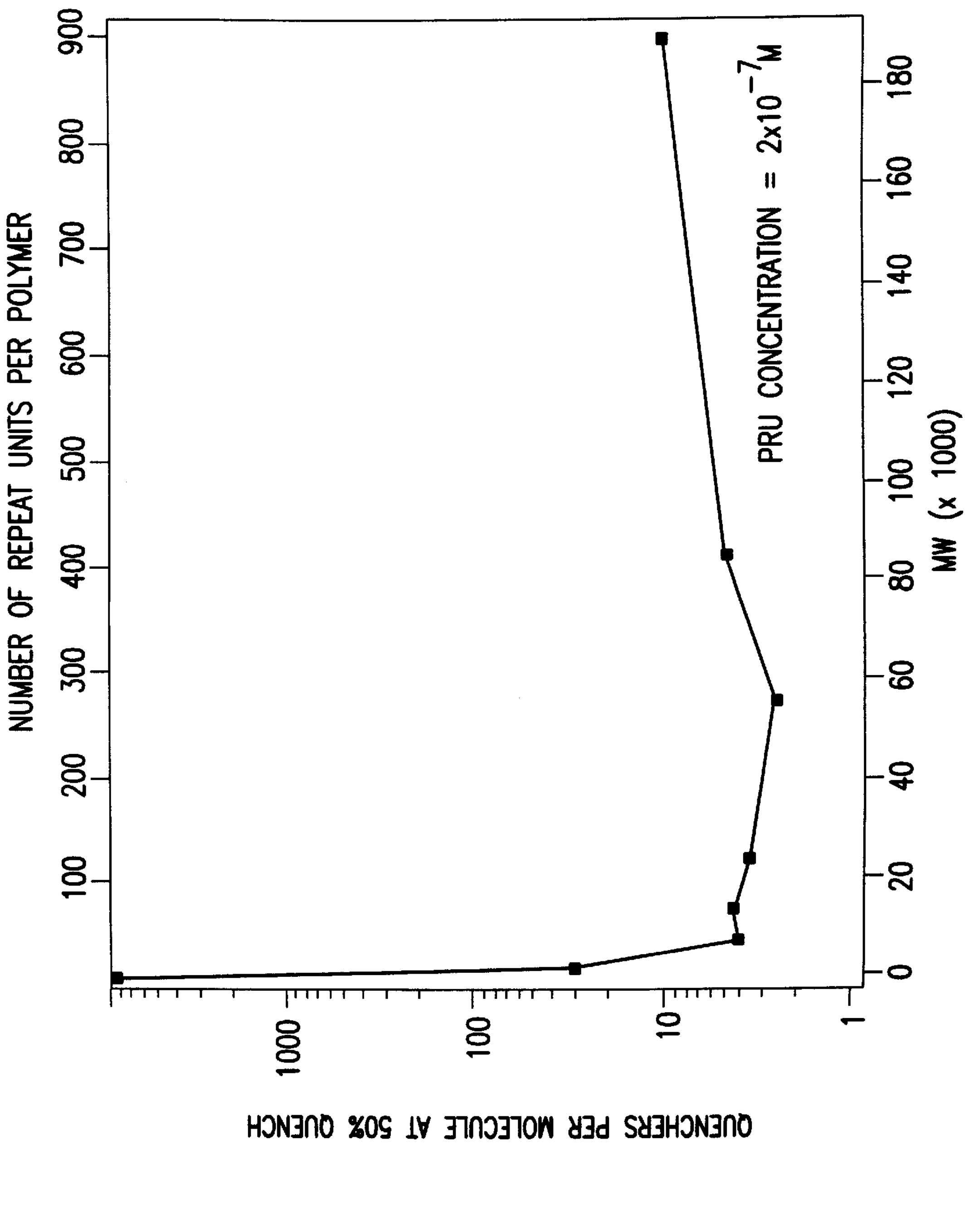
FIG. 8*b* is a logarithmic graph of the quenchers per polymer at 50% quenching as a function of polymer repeat units (PRU) set forth in FIG. 8*a*.
Figure 9A:
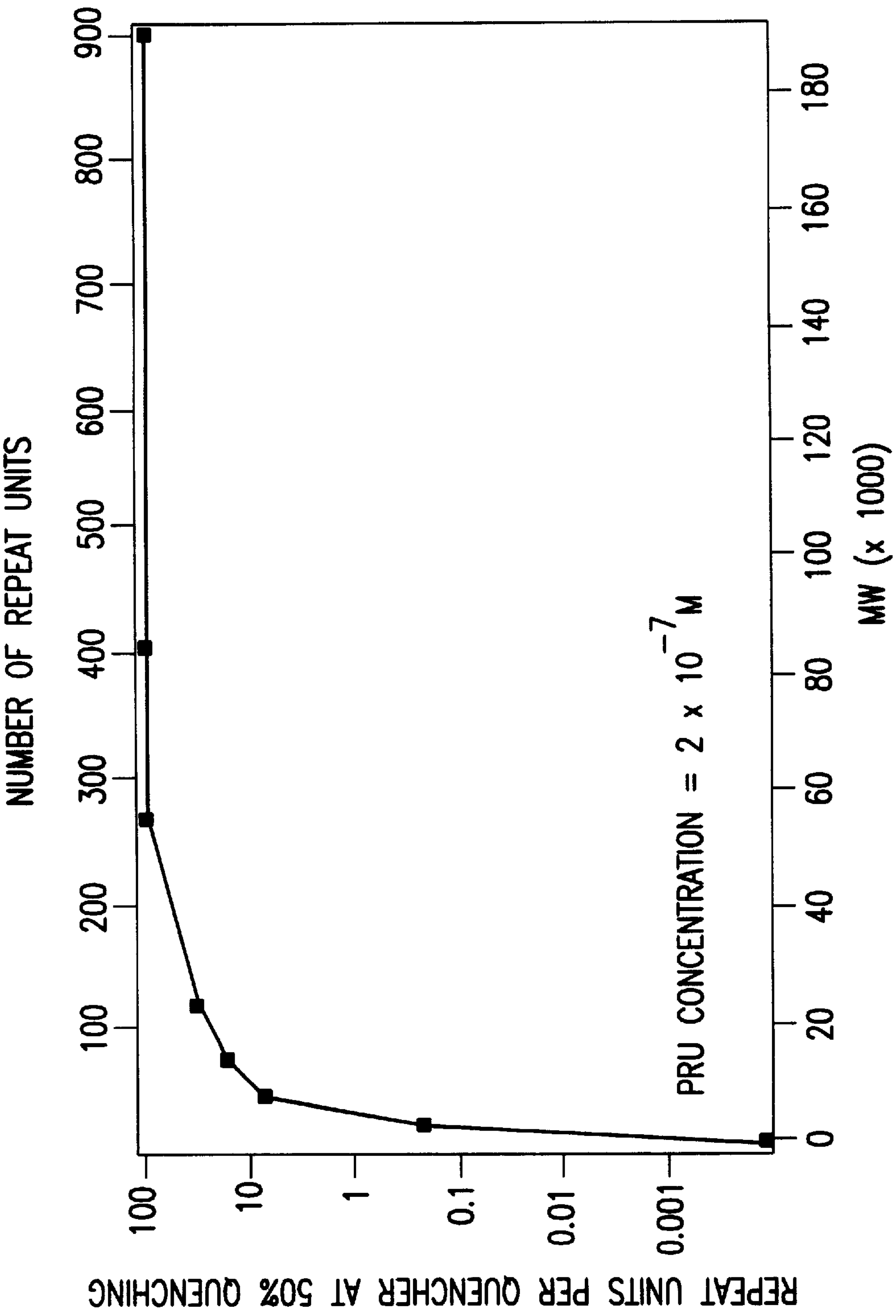
FIG. 9*a* is a graphical illustration of polymer repeat units/quencher as a function of polymer molecular weight.
Figure 9B:
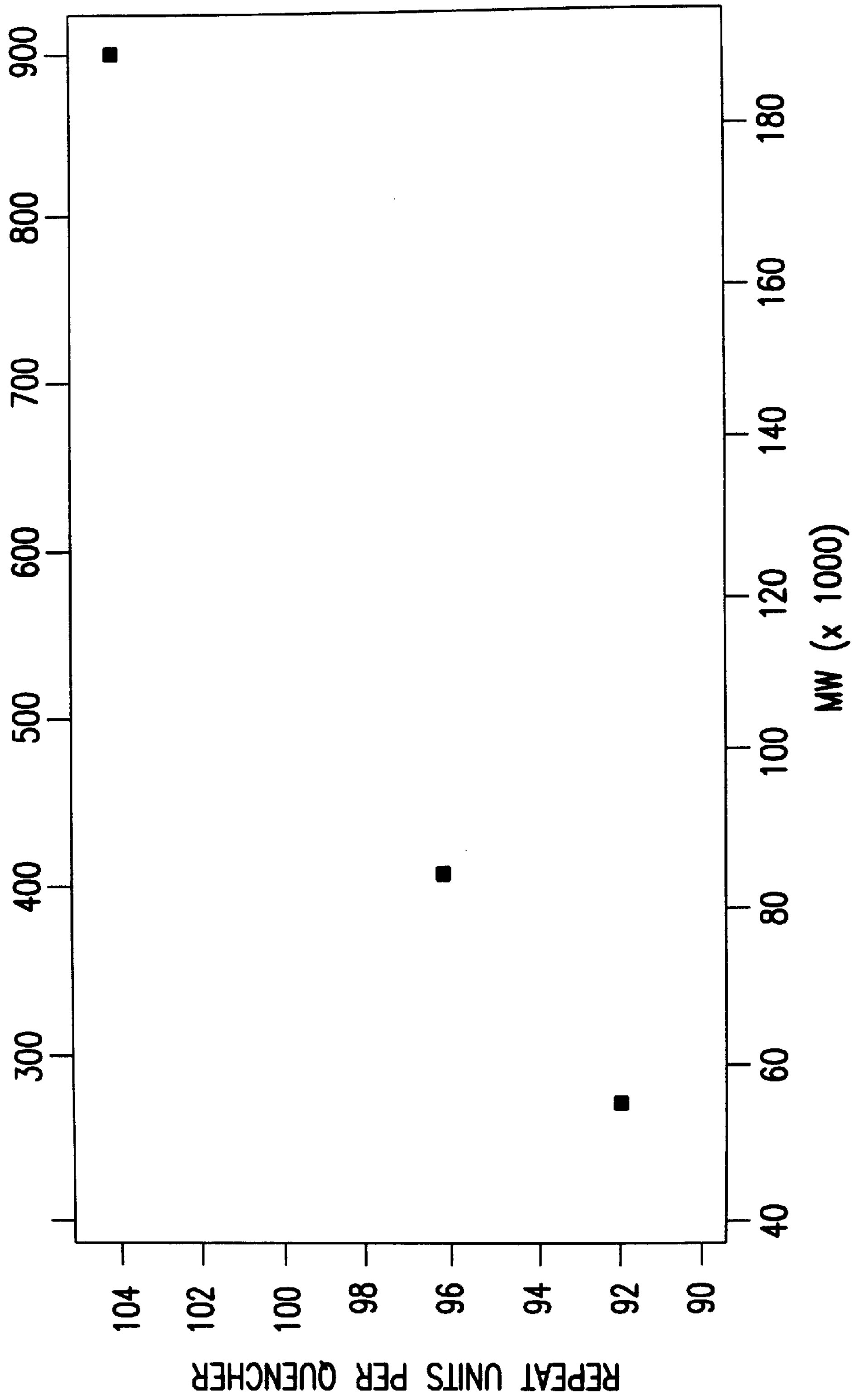
FIG. 9*b* is a logarithmic graph of the polymer repeat units/quencher as a function of polymer molecular weight set forth in FIG. 9*a*.

One specific J-aggregate polymer used in experimentation by the present inventors has a cationic cyanine dye on each repeat unit and thus is a polycation. (See FIG. 6*a*). A specific advantage of this polymer is that it is not subject to quenching by inorganic cations. The very short excited state lifetime of J-aggregated cyanines (less than 50 ps) also limits the possibility that the excited dye aggregate can be quenched by dynamic interactions with potential quenchers not associating with the polymer in the ground state. This polymer has been prepared in a variety of molecular weights ranging from monomer to small oligomer to polymers having a number of polymer repeat units (PRU) ranging from 6–904. In water and water-dimethylsulfoxide, the polymer exists predominantly as a J-aggregate when the number of PRUs exceeds 110. However, the fluorescence emission of the polymer arises from a J-aggregate for polymers having 33 PRUs or higher. Quenching of this series of polymers by the anionic electron acceptor, anthraquinone disulfonate in water and water-dimethylsulfoxide (50:50 volume:volume), shows that the extent of "superquenching" increases with molecular weight and the extent of J-aggregation (see Tables 1, 2 and FIG. 7). The values obtained for very dilute solutions of the polymers with 263, 401 and 904 PRUs for Ksv are $5\times10^{8}$–$1.2\times10^{9}$ $M^{-1}$ and are the highest known Stem-Volmer quenching constants. Although the smallest oligomer (5–6 PRU's) exhibits "superquenching", the extent of quenching can be enhanced by 2–3 orders of magnitude by increasing the number of PRU's and the extent of aggregation. Plots of quenchers per polymer and effective number of repeat units per quencher at 50% quenching indicate that the ideal size for use of the polymer in solution saturates at about 250 PRU (see FIGS. 8*a*, 8*b* and FIGS. 9*a*, 9*b*).

TABLE 1

Fluorescence Quantum Yields for Cyanine Dye Polymers at 22° C.

| MW of starting polylysine | PRU | DMSO/$H_2O$ (50%) | $H_2O$ | Lifetime | $X^2$ |
|---|---|---|---|---|---|
| 189,000 | 904 | 2.6% | 0.86% | 9 ps (95.0%), 57 ps (4.4%) | 1.23 |
| 84,000 | 401 | 2.5% | 0.70% | | |
| 50,000 | 263 | 2.0% | 1.0% | 9 ps (91.3%), 57 ps (8%) | 1.37 |
| 23,000 | 110 | 2.6% | 0.76% | | |
| 13,200 | 63 | 2.0% | 1.4% | | |
| 6,900 | 33 | 1.2% | 1.3% | | |
| 500–2,000 | 5~6 | 2.7% | 2.1% | 60 ps (51.6%), 255 ps (34.2%), 849 ps (13.5%) | 1.37 |
| monomer | 1 | 1.7% | 0.3%[a] | 152 ps (85.7%), 652 ps (14.3%) | 0.92 |

[a]The quantum yield of monomer in water is low due to the presence of J-aggregates.

TABLE 2

| Fluorescence Quenching of Cyanine Dye Polymers by Anthraquinone Sulfonate at 22° C. | | | | |
|---|---|---|---|---|
| MW of starting polylysine | PRU | $K_{SV}$ ($M^{-1}$) in DMSO/$H_2O$ (50%) | $K_{SV}$ ($M^{-1}$) in $H_2O$ | $K_{SV}$ ($M^{-1}$) in $CH_2Cl_2$ |
| 189,000 | 904 | $5.2 \times 10^8$ | $4.6 \times 10^8$ | $1.5 \times 10^7$ |
| 84,000 | 401 | $4.8 \times 10^8$ | | |
| 50,000 | 263 | $4.6 \times 10^8$ | $4.8 \times 10^8$ | |
| 23,000 | 110 | $1.6 \times 10^8$ | | |
| 13,200 | 63 | $7.5 \times 10^7$ | $5.5 \times 10^7$ | |
| 6,900 | 33 | $3.4 \times 10^7$ | $4.3 \times 10^7$ | $2.7 \times 10^7$ |
| 500–2,000 | 5~6 | $1.0 \times 10^6$ | | |
| monomer | 1 | 630[a] | | |

[a]The quenching constant of monomer in DMSO in about 55 $M^{-1}$.

Extensive studies of the quenching and unquenching of a J-aggregate polymer with 263 PRU's have been carried out both in solution and with the polymer adsorbed onto supports. In solution, this polymer is quenched by very small amounts of anionic electron or energy acceptors. The corresponding QTL conjugates with biotin and xanthines as the ligands show similar high quenching sensitivities of the polymer. The QTL conjugates quench the fluorescence of the polymer but relatively little unquenching is observed when the protein avidin is added to solutions quenched by the biotin QTL's. The failure to observe significant unquenching is attributed to the tendency of the 263 PRU cyanine polymer to associate strongly with neutral or charged biomacromolecules such as proteins and nucleic acids in aqueous solution.

J-aggregate polymers (which include but are not limited to CDP) offer the following significant and distinct advantages over conjugated polymers previously examined:

1. A J-aggregate polycation polymer should not be quenched or modified by inorganic cations (such as copper) at physiological concentrations. On the other hand, inorganic cations quench anionic conjugated polymers. Inorganic anions may bind to the J-aggregate polymer, but they should not affect fluorescence in most cases.
2. J-aggregate polymer structure is controlled and likely predictable based on the polypeptide backbone and is likely to be in an α-helix or β-sheet arrangement that should persist in a variety of media. The polymer structure for previously disclosed conjugated polymers varies widely in different media.
3. The J-aggregate polymer exhibits extremely sharp and intense absorption and fluorescence such that it can be used (and its fluorescence detected) at concentrations as low as $10^{-9}$ M in solution and even lower in other formats. The fluorescence line width is over 10 times narrower than that for previously disclosed conjugated polymers.
4. J-aggregate polymers should retain sharp and narrow absorption and fluorescence band properties in a variety of media and complex fluids. The absorption and fluorescence of conjugated polymers varies widely in different media.
5. J-aggregate polymer and polymer-QTL formats may be coated onto anionic surfaces without losing their J-aggregate absorption or fluorescence properties. The absorption and fluorescence of conjugated polyelectrolytes is drastically altered upon film formation.
6. Several different "color" J-aggregate polymers may be obtained by synthetic manipulation of the cyanine dye portion of the polymer repeat unit without changing the inherent structure of the polymer (i.e., it is controlled by the peptide backbone). In the visible spectrum, this will allow 10–15 distinct color bands in a single sample. Previously disclosed conjugated polymers only allow 2–3 distinct color bands in the visible spectrum.
7. The peptide-based polymers contain additional (terminal) functional groups that can be used to append the polymer to a ballast, support, or to a QTL unit. These functional groups are absent in previously disclosed conjugated polymers.
8. J-aggregate polymers can be readily synthesized in a variety of molecular weights varying the size and sensitivity of the polymer to quenching by various agents.

Supported Polymer-QTL Platforms for Bioagent Detection

1. Tethered Polymer-QTL (P-T-Q-T'-L) as Custom Agent Detectors

The fluorescent polymer-QTL approach to bioagent detection can be significantly improved by directly linking the polymer by a covalent tether to the QTL unit. In this way, a specific fluorescent polymer-QTL combination can be used at near single-molecule levels to detect a specific bioagent. The "molecular sensor"-P-T-Q-T'-L is constructed such that in the absence of the bioagent to be sensed, the fluorescence of the polymer (P) is quenched. Since electron transfer quenching is only effective through space over very short distances, the removal of the quencher away from the fluorescent polymer by only a few angstroms can result in an "unquenching" of the polymer fluorescence. In the absence of a receptor available for complexing with the ligand, the polymer will have the tethered quencher in close proximity and its fluorescence will be quenched. This concept is diagramed schematically below in Table 3.

TABLE 3

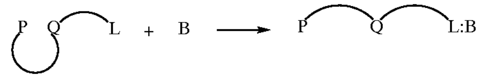

| | |
|---|---|
| Absence of bioagent (B): polymer fluorescence quenched due to ground state association of P and Q, | Addition of B results in association between L and B and pulls Q away from P, turning on the polymer fluoresence. |

Figure 10:
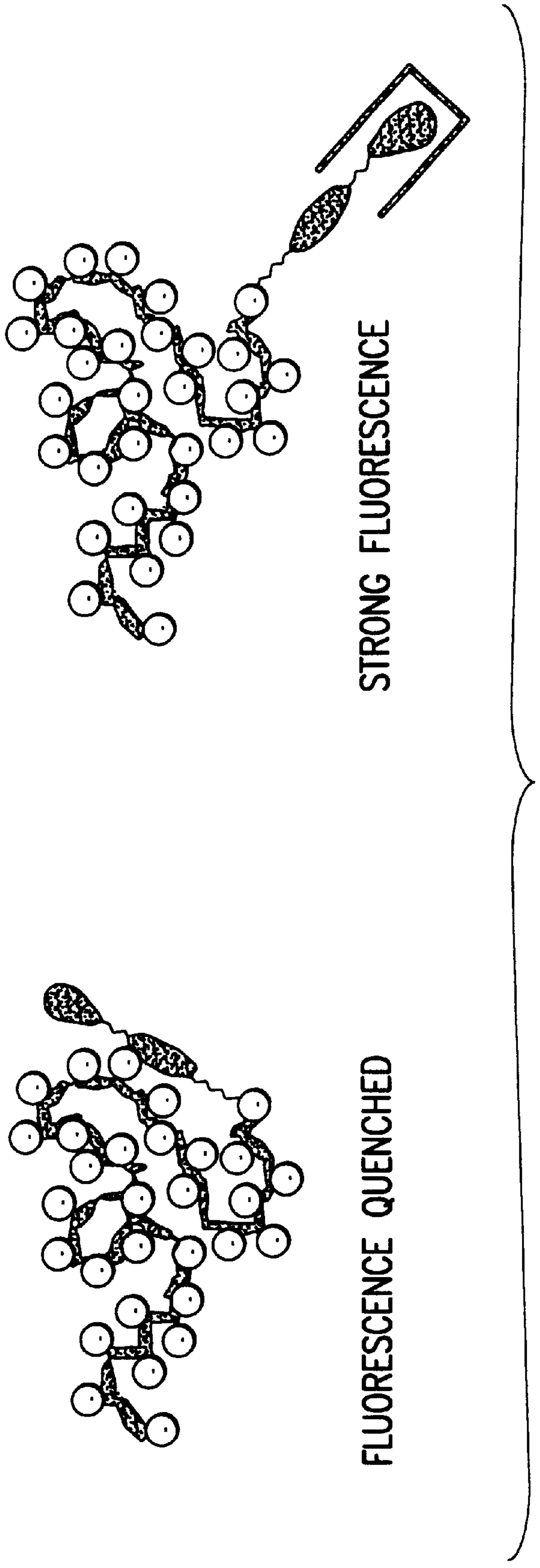
FIG. 10 is an illustration of the fluorescence "turn on" and "turn off" with tethered PTQT'L.
Figure 11A:
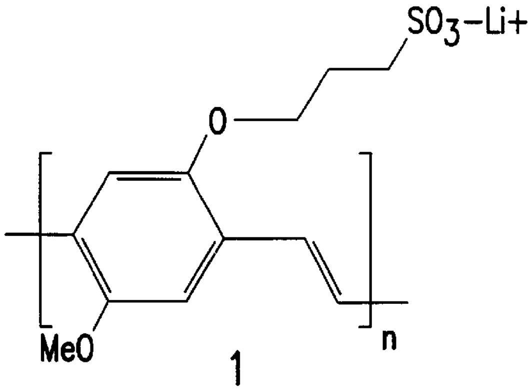
FIG. 11 is an illustration of various molecules used in QTL experiments.
Figure 11A:
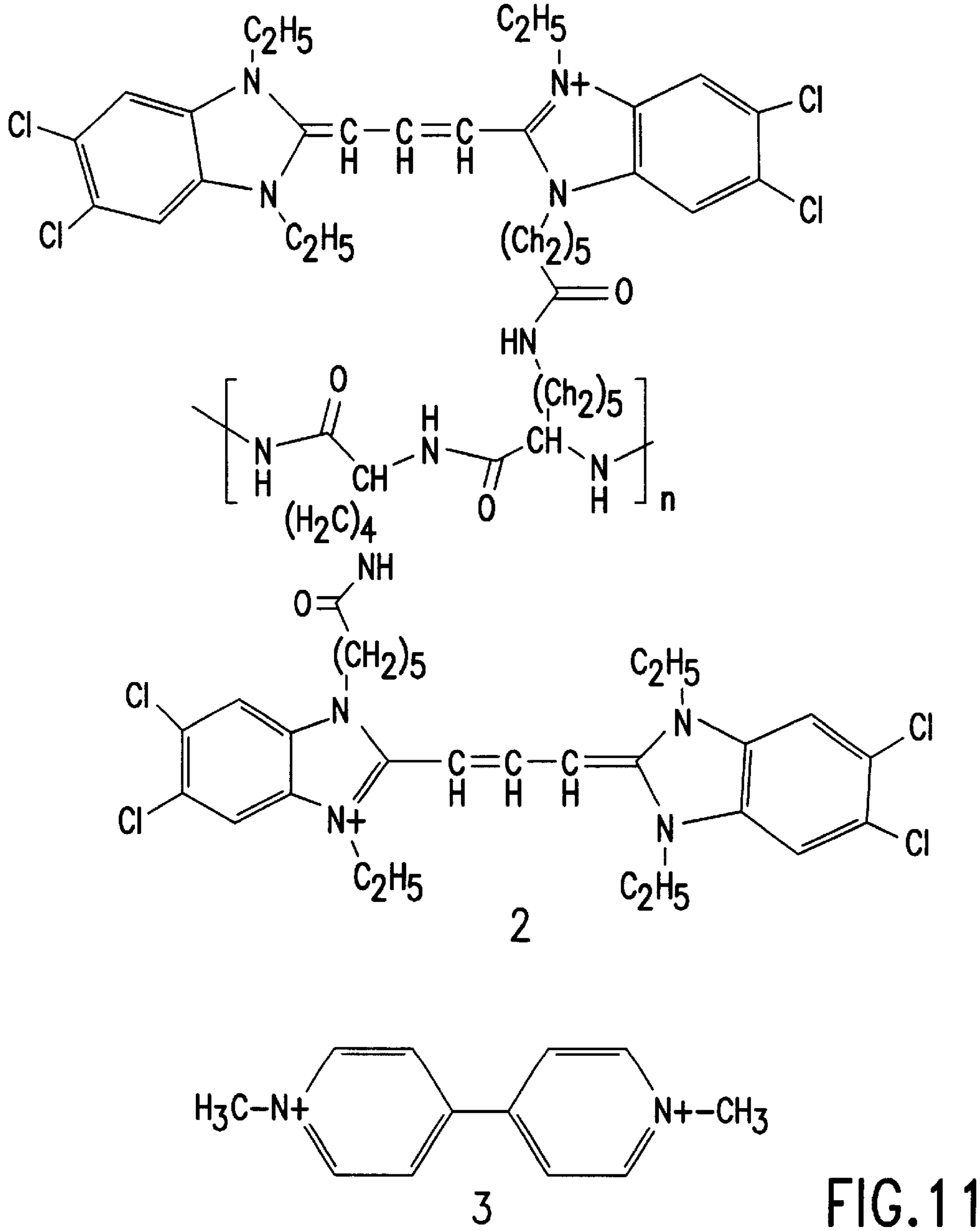
Figure 11B:
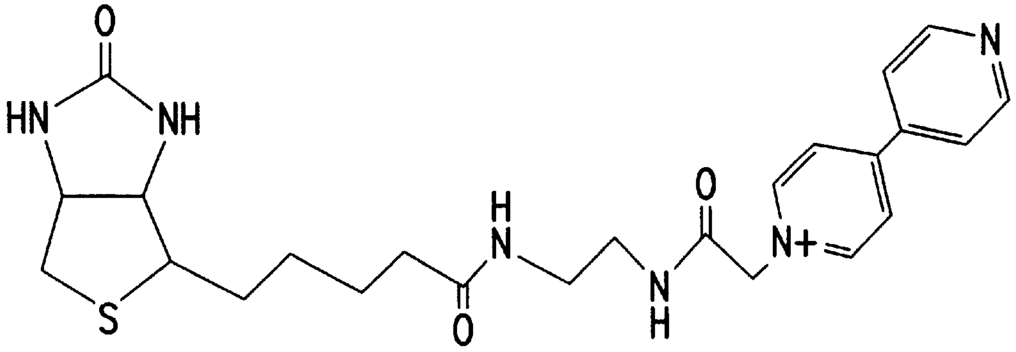
Figure 11B:
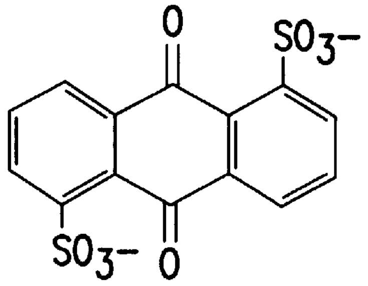
Figure 11C:
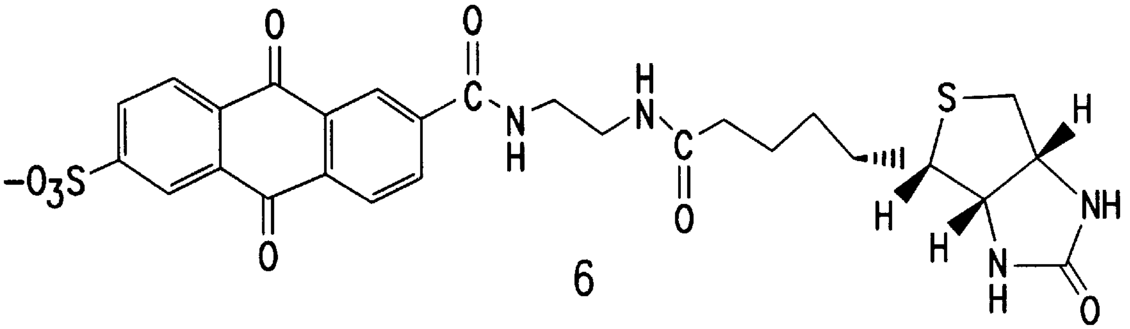
Figure 11C:
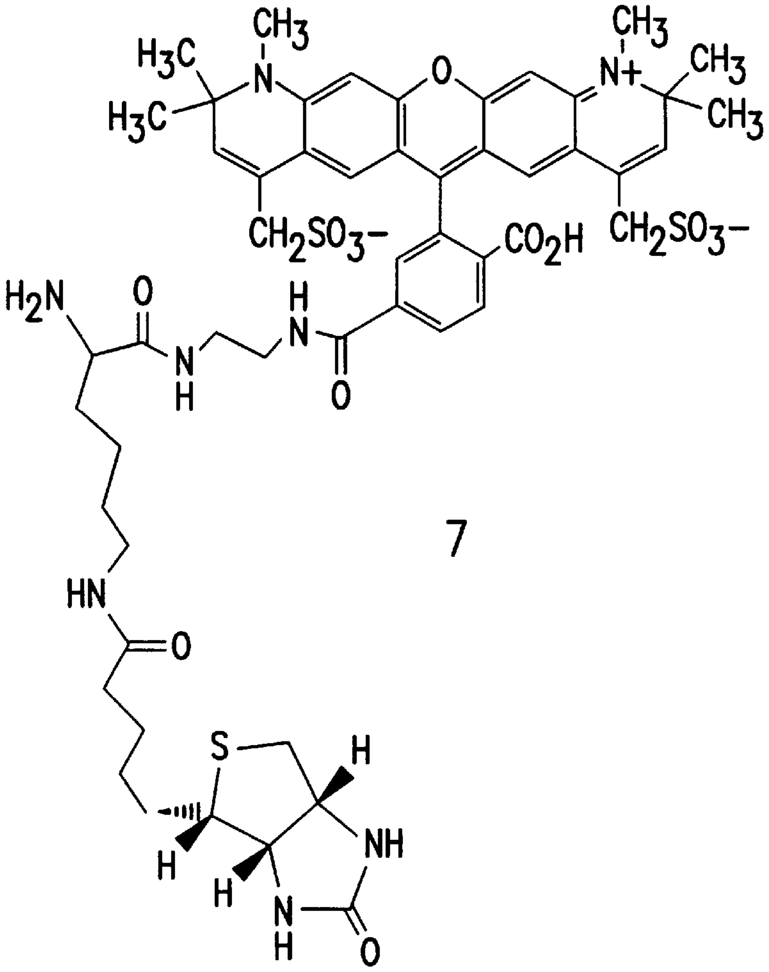

In aqueous or mixed aqueous-organic solvent environments, hydrophobic and coulombic (i.e., the quencher has opposite charge to the polymer) effects favor a "folded" configuration. As can be seen in FIG. 10, the addition of a receptor results in a "pulling away" of the quencher-ligand and "turns on" the polymer fluorescence. As discussed above, if the QTL molecule is precomplexed with a bioagent, addition of a natural or synthetic ligand can release the PTQT'L from the bioagent. Thus, the tethered format also provides a platform in which the polymer-QTL functions as a "turn-off" fluorescence assay, as shown in FIG. 10. The tether (T) linking the polymer (P) to the quencher (Q) is sufficiently flexible such that close approach of P and Q within the distance required for resonant energy transfer or electron transfer is possible. Examples of suitable tethers (T) include, without limitation, polyethylene, polyethylene oxides, polyamides, non-polymeric organic structures of at least about 7–20 carbon atoms, and related materials. The second tether (T') linking Q and the bioagent ligand (L) must be sufficiently short such that binding of bioagent (B) to the quenched polymer results in pulling the quencher away from the polymer and "turning on" the polymer fluorescence. The complex P-T-Q-T'-L:B is thus a fluorescent "tagged" bioagent and can be tracked and isolated by virtue of its fluorescence.

By developing a suite of P-T-Q-T'-L molecules where P and L are varied, it is possible to have polymers which fluoresce with different "colors" in response to the presence of specific agents. This provides a convenient means for analyzing for several agents in the same sample. The quencher to be used in this format will most preferably be a species that quenches in a non-radiative fashion and that exhibits a sharp fall-off of quenching efficiency with quencher-polymer separation. The most appropriate quenchers are those that quench the polymer fluorescence by electron transfer and that form weak ground state charge-transfer complexes. Examples of the polymer include, but are not limited to, fluorescent polymers (including conjugated polymers), conjugated polyelectrolytes and J-aggregating dye polymers (including polyelectrolytes). The J-aggregating dye polyelectrolytes presently offer the best possibilities for synthesis of a suite of molecules for multiplexing due to the narrow spectral band of emission in these polymers.

PTQT'L can be used to assay several different ligand-receptor combinations including, but not limited to, hormone-protein (and other small molecule-receptor combinations), protein-protein, polypeptide-protein, and glycolipid-protein.

It should be noted that for all of the above-described applications, the fluorescent polymer may be most conveniently employed when it is anchored either covalently or by ionic adsorption onto a support such as a bead or plate and used in either a static or flow-through mode.

2. Anchored Polymer-tethered QTL Systems for Bioagent Detection

A second variation of the tethered polymer platform involves the use of a totally anchored polymer: QTL unit on a surface, probe, or bead. This format is especially convenient for both detection and isolation of a bioagent. In this format, a unit much like the P-T-Q-T'-L is itself anchored either covalently or non-covalently on a surface, bead, or other support by covalent or non-covalent linkages. Addition of a bioagent (B) that binds with L increases the separation between P and Q and reverses the quenching that is observed in the absence of B. In this format, the binding of the bioagent both anchors it to the surface where the polymer-quencher-ligand species is isolated and turns on the fluorescence of the polymer.

The same restrictions on the quenching nature of Q discussed above with respect to a tethered polymer-QTL (P-T-Q-T'-L) system also apply to anchored polymer-tethered QTL systems. The advantage is the simultaneous detection and immobilization of the bioagent on the surface containing the polymer-quencher-ligand reagent. This format can be used for both liquid samples and aerosols and may be used for continuous monitoring of streams of liquids or vapor. The addition or flowing of a stream of bioagent "recognizing" the specific QTL molecule results in the removal of the bioagent from the stream and the "turning on" of the polymer fluorescence. This concept is diagramed in Table 4.

TABLE 4

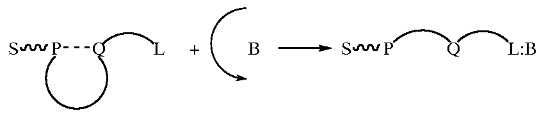

| | |
|---|---|
| Absence of bioagent (B): polymer fluorescence quenched due to ground state association of P and Q, An aerosol or liquid containing B flows over the surface containing the polymer-quencher-ligand. | Capture of B results in association between L and B and separation of Q and P, turning on fluorescence from the polymer immobilization of B. |

When combined with anchored polymer+QTL formats, a very powerful way of simultaneously detecting several bioagents and reducing the chances of "false positives" is provided. By placing the various tethered polymer-QTL's in different wells or on photodiodes in a multi-well plate or photodiode array, a large number of compounds or samples may be assayed at one time. This is a useful application in the high-throughput screening of drugs and in clinical medical diagnostics.

Many of the same phenomena observed in solution can also occur in interfacial and supported formats. Additionally, the use of supported or combined formats allows a remarkable tuning, and in some cases, enhancement of superquenching that offers powerful advantages for biosensing applications. In many instances, coating the fluorescent polyelectrolyte onto a surface of a bead or particle is effectively irreversible such that the material is not removed, even on repeated washings.

Figure 12:
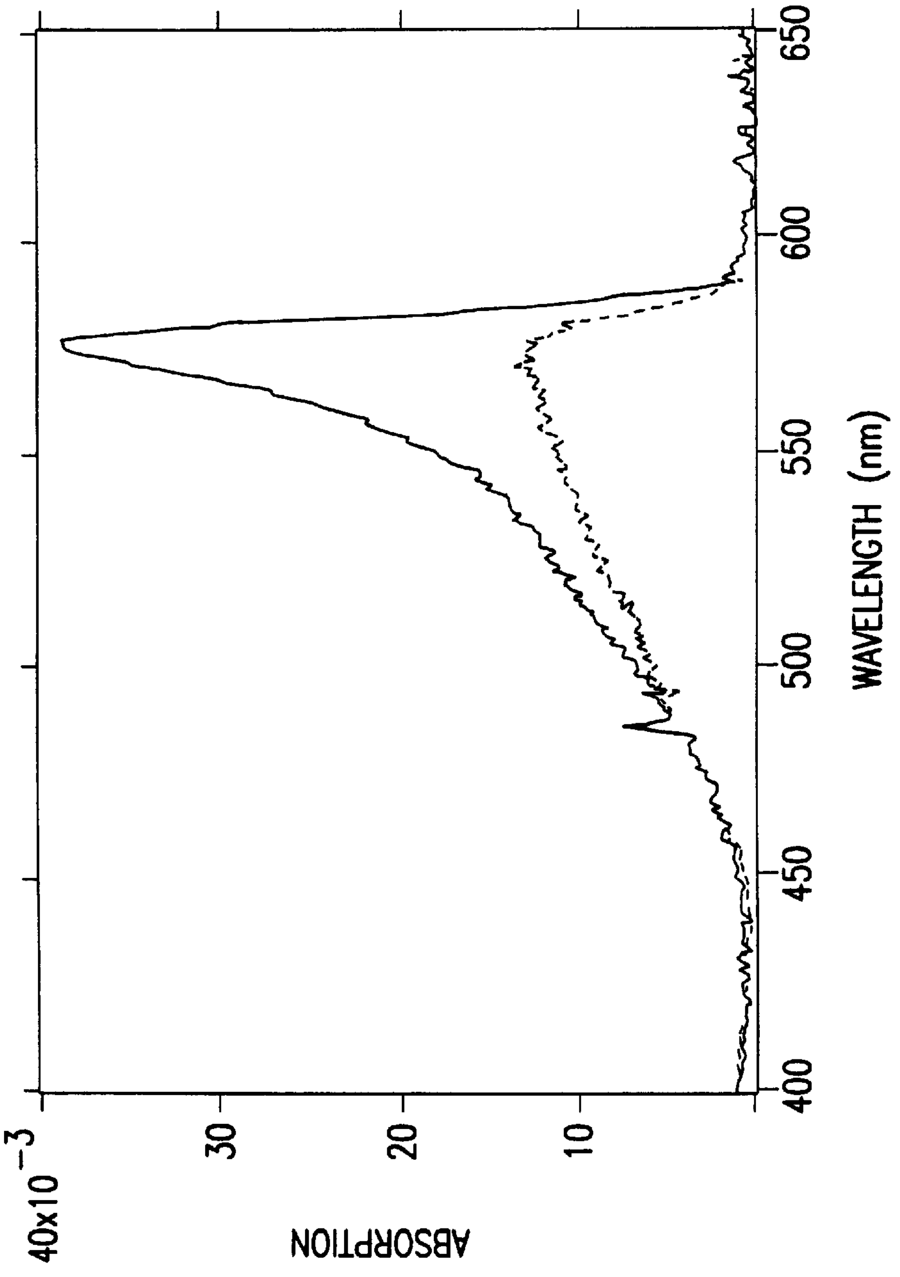
FIG. 12 is a graphical illustration of the absorption spectra of polymer 2 free in solution (solid line) and adsorbed onto clay (dotted line).

It was recently reported that CDP polymer 2, shown in FIG. 11, can be adsorbed onto glass slides coated with Laponite clay. (See Place et al., Langmuir (2000) 16:9042). In this format, the polymer exhibits J-aggregation similar to that observed for the polymer in solution. It has now been determined that polymer 2 can be transferred to laponite clay suspensions in solution. In this case, although the polymer exhibited an absorption spectrum that is somewhat blue-shifted as compared to the J-aggregate in solution (see FIG. 12), it still exhibited chromophore aggregation characterized by a red-shift from the monomer spectrum. In the supported format, the quenching charge reversal may be tuned by adjusting the level of coverage of the polymers on the clay particles. Although from size and charge considerations it is expected that the clay would take up several molecules (perhaps as many as 20) of polymer 2 per particle, careful titration of the dye with clay indicated that the number of polymer molecules adsorbed per particle may be much lower (see Jones et al., Langmuir (2001) 17:2568–2571). Titration of the dye with Laponite suspensions until no additional uptake of polymer occurred resulted in very small changes in light scattering from dissolved polymer 2 to Laponite-supported polymer 2, suggesting that each clay particle bears at most a small number of polymer molecules or an average of about one polymer molecule per clay particle. Under these conditions, the supported polymer 2 exhibited moderately enhanced superquenching by the anionic anthraquinone 5 ($Ksv=1.1\times10^{8}\ M^{-1}$) as compared to aqueous solutions of the same substrate and quencher ($Ksv=7\times10^{7}\ M^{-1}$).

In addition, it was recently reported that polymer 2 in solution could be quenched by the anthraquinone-biotin conjugate 6, illustrated in FIG. 11, but was not "unquenched" upon the addition of avidin, presumably due to the strong association of avidin and polymer 2. (See Jones et al., Supra). Remarkably, it has been discovered that the use of polymer 2 in the clay supported format described above allows both enhanced superquenching by anthraquinone-biotin conjugate 6, as well as quantitative "unquenching" upon the addition of avidin. Therefore, the use of supported formats permits a reduction of the sensitivity of the polymers to nonspecific interactions with proteins and at the same time allows polymer-quencher interactions to be tuned. In this way, the anionic bioconjugate 6 can be used to demonstrate the quench-unquench biosensing by specific binding and removal of the bioconjugate by its receptor.

When polymers 1 and 2 are mixed together in dilute aqueous solution there is clear evidence of energy transfer from the higher energy excited states of polymer 1 to the lower energy emitting J-aggregate state of polymer 2. This interpolymer energy transfer can be observed at very low concentrations and can be reasonably assigned to association between the two polymers. Although the predominant fluorescence of an ensemble formed from an equimolar (in repeat units) mixture of the two polymers is from the J-aggregate band of polymer 2, the addition of cationic viologen 3 illustrated in FIG. 11 results in a quenching of the fluorescence. The fluorescence of the ensemble is also quenched by the addition of anionic anthraquinone 5. Thus, the fluorescence of the ensemble can be quenched by both cationic and anionic electron acceptors and the photophysical properties of the individual polymers are strongly coupled. The quenching by both cations and anions suggests that while the ensemble is overall near neutral, individual regions of each polymer possess sufficient residual charge to strongly bind small counterions and permit superquenching by both cationic and anionic quenchers.

While the use of mixtures may provide a means for gaining enhanced quenching, it is also desirable to be able to use mixtures of fluorescent polymers in applications where their individual behavior is retained. This has been accomplished by using a format where one of the two polymers is supported and the other remains in solution. In particular, it was discovered that coating of polymer 2 onto Laponite clay followed by the addition of polymer 1 in an aqueous solution lead to a mixture that demonstrated independent behavior of the two polymers both with respect to their fluorescence and to fluorescence quenching. The fluorescence of this mixture with no quenchers added was the simple sum of the fluorescence of each polymer individually, i.e., no energy transfer or fluorescence quenching is observed. The addition of viologen 3 to this mixture only quenched the fluorescence of polymer 1, while addition of an anion, i.e., anionic anthraquinone 5, to the mixture resulted in the selective quenching of the fluorescence of polymer 2. This indicates that the use of a supported format may allow the simultaneous sensing of different antigens by several different polymers in the same suspension.

By layering fluorescent polyelectrolytes onto oppositely-charged surfaces, superquenching effects may be tuned, nonspecific interactions may be eliminated, and the use of fluorescent polyectrolytes in quantitative bio assays may be optimized. Also, mixtures of oppositely-charged polyelectrolytes offer a means of both charge-tuning and enhanced light harvesting by energy transfer.

Detection of Chemical and Biological Agents Using Electrophoretic Dye Polymer-QTL Combinations 1. Electrophoretic Fluorescent Polymer QTL Combinations for Bioagent Detection The fluorescent polymer-QTL approach to bioagent detection can be greatly expanded in terms of scope of detection by using an electric field-assisted separation of the QTL-bioagent complex from the fluorescent polymer. A variety of polymers and QTL reagents have been developed such that in the absence of an agent and an electric field, the fluorescence of the polymer is quenched by the formation of a complex between the polymer and the QTL.

TABLE 5

P---Q-T-L + B ⟶ P + Q-T-L:B

Conventional QTL:

| Absence of Bioagent: Polymer fluorescence is quenched by complex formation with QTL. No fluorescence is detected or the fluorescence of Q or a Polymer-QTL complex may be detected | Addition of Bioagent: The strong association between L and B results in a new complex that is too large to permit the Polymer-QTL association and the QTL is pulled away from the polymer resulting in a "turn on" of the polymer fluorescence. |
|---|---|

In the QTL-based bio sensors discussed above, the complex between the polymer and the QTL molecule is broken by the formation of a complex between the ligand L and the bioagent, B. (See Table 5). This scheme works well for bioagent-ligand combinations where the ligand is much smaller than the bioagent-ligand complex. However, often times, the ligand and bioagent will be of comparable size such that the resulting steric effect on binding of the ligand to the bioagent is not sufficient enough to result in the breaking of the polymer-QTL association. In these cases, an electric field may be used to dissociate the polymer from the bioagent-QTL complex. The electric field effect takes advantage of the fact that the fluorescent polymer to be used is a polyelectrolyte (either polycation or polyanion) and the bioagent to be detected (e.g., protein, nucleic acid, or larger complex biomolecule) will in general also have a large positive or negative charge.

In contrast, the QTL molecule used in electrophoretic detection will usually be a simple mono or divalent cation or anion. For this simplest electric field-assisted QTL detection, it is necessary to select a polymer of opposite net charge from the bioagent to be detected. By studying the electric field effect on solutions, bilayers, or gels containing the polymer-QTL complex, it can be determined how strong a field must be applied to promote the separation of the polymer-QTL complex. This field will generally be much stronger then that necessary to separate the polymer or bioagent. Thus, in the absence of an applied electric field, the addition of the bioagent will result in complex formation between the polymer-QTL and the bioagent (i.e., polymer-QTL:B). However, upon application of an electric field, the polymer and the bioagent-QTL will separate and the fluorescence of the polymer will be regenerated as the quencher is removed. If the quencher portion of the QTL is fluorescent, its fluorescence may also be detected at an independent wavelength when the electric field is applied. The effect of the electric field is shown below schematically in Table 6.

TABLE 6

$P^{(n+)}$--QTL + $B^{(m-)}$ ⟶ $P^{(n+)}$--QTL:$B^{(m-)}$

Electric Field Assisted QTL: No Applied Field

| Absence of Bioagent: Polymer fluorescence is quenched by | Addition of Bioagent: The strong association between L and B results |
|---|---|

TABLE 6-continued

| | |
|---|---|
| complex formation with QTL. No fluorescence is detected or the fluorescence of Q or a Polymer-QTL complex may be detected | in a new complex that consists of oppositely charged polymer and bioagent components. In the absence of an electric field the fluorescence of the polymer remains quenched. |
| Electric Field Applied: | |

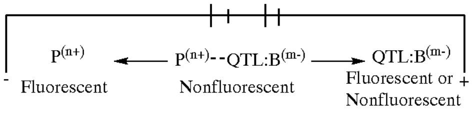

The electric field applied may be either AC (alternating current) or DC (static). In the former, the fluorescence generated by transient cleavage of the polymer-QTL:B complex may be observed as a modulation of the fluorescence signal corresponding to the frequency of the AC. If the applied field is DC, macroscopic separation of the complex may be achieved by conventional electrophoretic techniques. The combination of electrophoresis employing a modulating field with fluorescence detection offers the advantage of sensitive detection with the ability to distinguish between specific and non-specific binding events.

2. Electrophoretic Fluorescent Polymer-tethered QTL Combinations for Bioagent Detection Tethered polymer-QTL formats (P-T-Q-T'-L) may also be used in an electrophoretic format with similar advantages to those discussed above for the "simple" polymer-QTL approach to biosensing. In this case, the tethered polymer-QTL complex will be quenched in the "resting mode" (i.e., no bioagent and no applied electric field) provided that the tether is sufficiently "flexible" to permit the folding of the quencher to a configuration permitting near or close contact with the polymer. Application of an applied AC or DC field may result in transient or permanent separation, respectively, of the polymer and tethered QTL provided that the polymer and QTL components have a substantially different net charge. As shown in Table 7, fluorescence is absent in the absence of an AC or DC field and "turned on" by the application of a sufficiently strong AC or DC field to pull the QTL and polymer apart.

TABLE 7

| | |
|---|---|
| 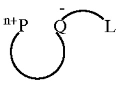 | 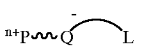 |
| No Electric Field: Fluorescence Quenched | Electric Field Applied: Fluorescence Observed |

Addition of the bioagent will result in complex formation but will not necessarily result in sufficient separation of the QTL:B complex from the polymer to "unquench" the polymer fluorescence. However, application of an applied AC or DC field will result in transient or permanent separation and the AC or DC field necessary to affect the separation will generally be much different (usually smaller) than that required to separate the polymer and QTL in the absence of B. (See Table 8). Thus, the electrophoretic effect can be used reversibly to sense specific bioagents.

TABLE 8

| | |
|---|---|
| 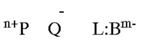 | 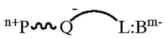 |
| No Electric Field: Fluorescence Quenched | Electric Field Applied: Fluorescence Observed |
| Presence of Bioagent: Fluorescence Quenched in absence of field, unquenched when field is applied but the field response (either AC or DC) will be much different in presence and absence of B. | |

3. Electrophoretic Anchored Polymer-QTL Combinations

The electrophoretic mode of bioagent detection may be used effectively in gels, bilayers, or solutions in formats where the fluorescent polyelectrolyte is tethered to a support in contact with the medium. In one embodiment, the polymer is tethered to the support and the QTL unit associates with the polymer through non-covalent interactions to quench the polymer in the absence of an applied electric field and bioagent. Applying the field in sufficient strength will cause the charged QTL component to migrate with a consequent "unquenching" of the polymer fluorescence. Addition of the bioagent to be detected in the absence of an electric field may or may not cause "unquenching" of the polymer fluorescence, depending on the size and steric effect resulting from bioagent-ligand complexation. However, even if there is no "unquenching" of the polymer fluorescence in the absence of an electric field, application of an electric field will result in the migration of the bioagent-QTL complex, a reversal of the fluorescence quenching and detection of the fluorescence from Q in the case where Q is itself fluorescent.

In general, the charge on the bioagent is different and much larger than the charge of the QTL molecule, and migration of QTL:B in the electric field is very different from that of a QTL molecule alone and is very easy to detect by fluorescence or colorimetric assay. As set forth above, the detection of specific, known bioagents will be easy and reliable due to the ability to predict the migration pattern at specific field strengths. The ability to tether the polymer to the surface should enhance the ability to separate the polymer and "tagged" bioagent and to use "flow formats" and the polymer reversibly.

4. Electrophoretic Anchored Polymer-tethered QTL Combination

As described above, formats using a polymer tethered to a QTL molecule and a polymer tethered to a support offer advantages for specific detection/isolation applications and for reversible operation of the biosensor. Electrophoretic/fluorescence sensing using a format with the tethered polymer-QTL itself tethered to a support in a bilayer, gel, or solution offer some additional advantages. In the absence of an electric field and bioagent, the tethered polymer-QTL quenches the polymer fluorescence. The addition of the bioagent to form a QTL:B complex may or may not result in the "unquenching" of the polymer fluorescence. In cases where no "unquenching" occurs, application of an electric field (i.e., AC or DC) can result in unquenching either in the presence or absence of bioagent. However, field strengths will be very different for the two cases. Furthermore, at some limiting electric field strength, it should be possible to remove the bioagent thus rendering the tethered polymer-QTL reusable.

Having generally described this invention, a further understanding can be obtained by reference to certain specific examples which are provided herein for purposes of illustration only and are not intended to be limiting unless otherwise specified.

EXAMPLE 1

Cyanine Polymer/QTL Approach

Figure 13:
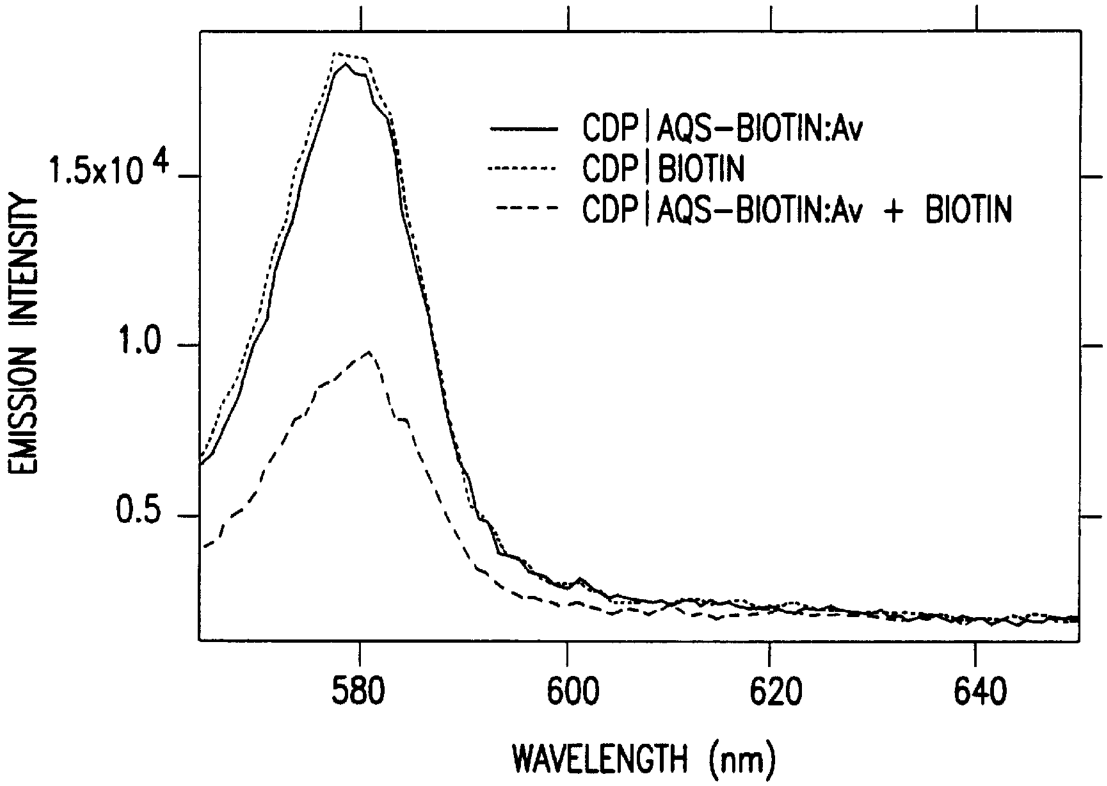
FIG. 13 shows a demonstration of a competitive assay with a J-aggregated CDP and a biotin-anthraquinone QTL conjugate.

A preferred embodiment for using a cyanine polymer/QTL approach consists of a competitive assay based on selective quenching of a cyanine polymer solution. For example, a 263 polymer repeat unit (PRU) cyanine polymer can be conveniently used in a fluorescence quench competitive bioassay. A competitive assay involving the avidin-biotin receptor-ligand system was conducted as follows: 500 μl of 0.1 μM of this polymer was added to the filtrate (lower) chamber of each of 3 separate Microcon YM-30 centrifugal filter vials. In each of these devices the filtrate chamber is separated from the retentate (upper) chamber by a 30 kilodalton (KD) nominal molecular weight cutoff (NMWCO) cellulose membrane. This membrane is impermeable to the 66 KD protein avidin but allows the biotin-anthraquinone conjugate to pass. A competitive assay was demonstrated by first complexing the anthraquinone-biotin QTL with avidin in a molar ratio 0.8:1 (QTL conjugate:avidin). Since each avidin has four biotin binding sites, this sub-stoichiometric ratio ensures full binding of all QTL conjugate to avidin. The three retentate chambers were charged with a.) 0.5 μM D-Biotin, b. and c.) 0.8 μM AQS-biotin conjugate complexed with 1.0 μM avidin. The 3 tubes were then each sealed and incubated for 10 minutes, after which time 0.5 μM D-Biotin was added to vial c. All three vials were then centrifuged for 1 minute at 12,000 g to allow permeable species in the retentates to mix with the filtrate containing the cyanine polymer. The fluorescence emission of all three filtrates was then measured at 20.0° C.+/−0.1° C. on a SPEX FluoroMax-3. Upon centrifugation, the biotin-avidin complex did not pass through the membrane, and no quenching was observed when only the avidin-QTL conjugate sample (vial b) was centrifuged. Also, no quenching was observed if only biotin (vial a) is present. As shown in FIG. 13, upon adding biotin to the QTL-avidin solution in a 4:1 ratio (biotin:avidin), competition of biotin with the biotin-anthraquinone QTL conjugate for the avidin binding sites resulted in release of the QTL, and subsequent to passage of QTL through the membrane quenching occurred.

EXAMPLE 2

Anchored Polymer-tethered QTL Approach

In an aqueous solution, anionic polymer 1 illustrated in FIG. 11 is strongly quenched by cationic electron acceptors such as methyl viologen (Formula 3 illustrated in FIG. 11) or the viologen-biotin conjugate, Formula 4, shown in FIG. 11. (Chen. L.; McBranch. D. W.; Wang. H.-L.: Helgeson R.: Wudl. F.: Whitten, D. G. Proc. Natl. Acad. Sci. 1999, 96, 12287–12292: Whitten, D.; Chen, L.; Jones, R.; Bergstedt, T.; Heeger, P.; and McBranch, D. in "Sensors and Optical Switches", Molecular and Supramolecular Photochemistry Vol. 7, Eds. K. S. Schanze and V. Ramamurthy, Marcel Dekker, Inc. Pub. In press).

As shown previously, the "unquenching" observed when the protein avidin is added to quenched solutions of polymer 1 complexed with QTL 4 provides a quantitative assay for the sensitive detection of a protein. Similarly, the cationic cyanine polymer 2 exhibits superquenching with the anionic anthraquinone disulfonate 5 and the corresponding conjugate 6, chemical structures are depicted in FIG. 11. (Jones et al., Supra). (Jones, R. M.; Bergstedt, T. S.; Buscher, C. T.; McBranch, D.; and Whitten, D. Langmuir, in press.) The inventors have examined quenching with this series of polymers and quenchers when the polymers are adsorbed onto oppositely charged supports. In particular, polymers 1 and 2 were coated from aqueous solution onto commercial (Pharmacia) cationic (Source 30 Q-average size, 30 microns) and anionic (Source 30 S) polystyrene beads, respectively. The coating of the beads with the polymers proceeded as follows: Beads were loaded into a 0.45 μm ultrafiltration tube and washed 3 times with water under gentle centrifugal force (100 g) to remove preservative. The beads were then resuspended in a polymer solution of known volume and concentration and then incubated for 1 hour at room temperature. Separation of free unadsorbed polymer from polymer-coated beads was effected by centrifugation for 3 minutes at 100 g. The coated beads were then washed 3 times with water to remove passively adsorbed polymer before they were stored as an aqueous suspension at 4° C. In each case, a "charge reversal" for the quenching of the supported polymers was observed. Thus, polystyrene-supported polymer 2 was quenched by viologen 3, but not by the anthraquinone sulfonate 5 and polystyrene-supported polymer 1 was quenched by anthraquinone sulfonate 5 but not by viologen 3.

Figure 14:
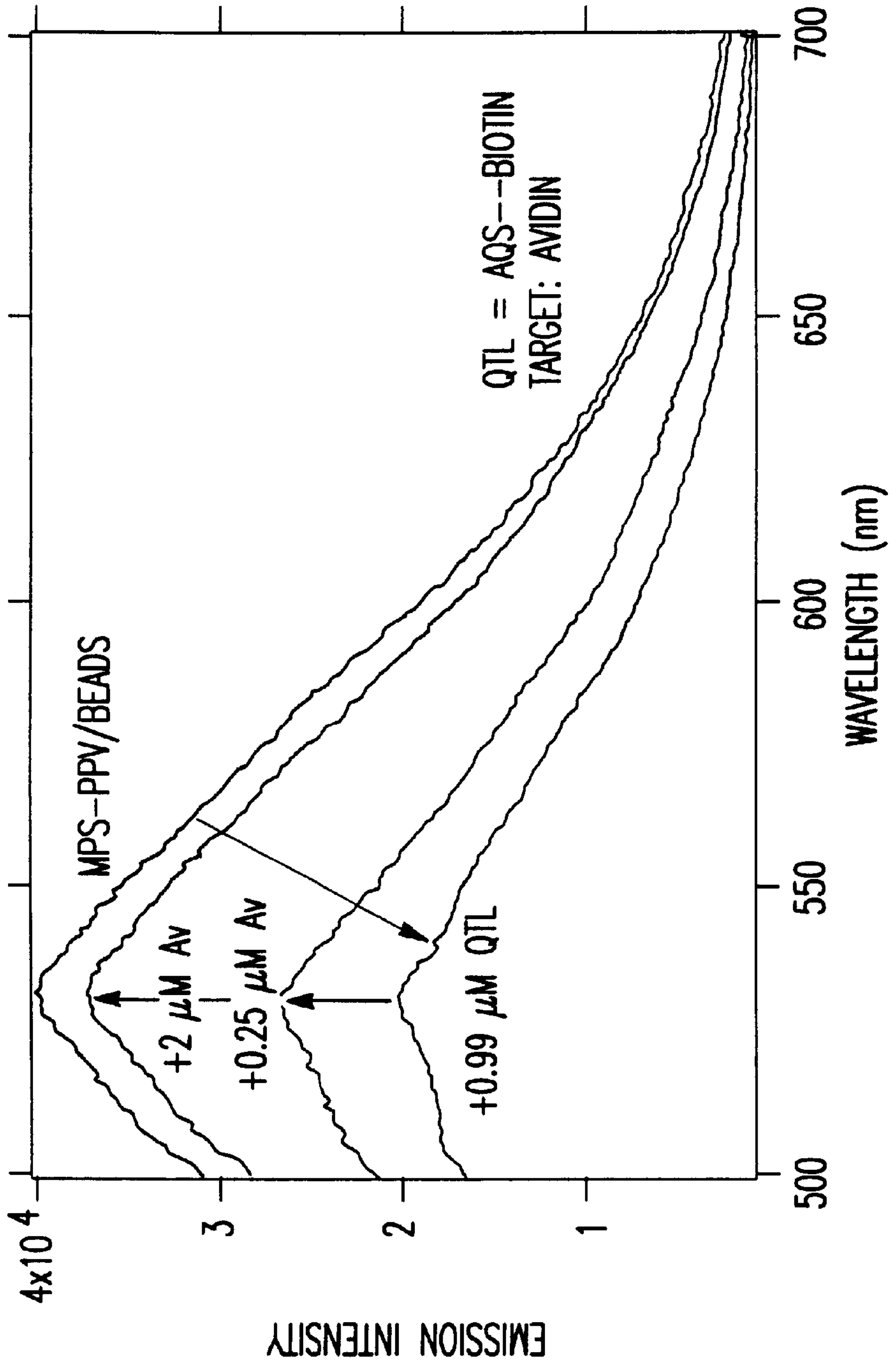
FIG. 14 is a graphical illustration of the emission spectra of polymer 1 coated onto microspheres: unquenched polymer (solid line), AQS-biotin conjugated quenched polymer 6 (dashed line), and Avidin quench recovered polymer (dot-dashed line).

The effect of the charge reversal on the quenching of the supported polymers extends to quenching-unquenching applications. Polystyrene-supported polymer 1 was quenched by the anionic anthraquinone-biotin conjugate 6 and addition of avidin resulted in a regeneration of the polymer fluorescence (see FIG. 14). Addition of avidin to unquenched polystyrene-supported polymer 1 resulted in no detectable change in the polymer emission and there was no fluorescence recovery when avidin was added to suspensions of polystyrene-supported polymer 1 that have been quenched by anthraquinone sulfonate 5. The fluorescence of polystyrene-supported polymer 1 was also quenched by the anionic dye-biotin conjugate 7, illustrated in FIG. 11. In this case, the quenching of the polymer fluorescence occurs via energy transfer and accompanying the quenching is a sensitization of the fluorescence of the dye-biotin conjugate 7. A quantitative "unquenching" of the polymer fluorescence can be obtained by adding an avidin solution to a suspension of the quenched polymer, this indicating removal of the conjugate from the supported polymer.

The invention of this application is described above both generically, and with regard to specific embodiments. A wide variety of alternatives known to those of ordinary skill in the art can be selected within the generic disclosure, and example are not be interpreted as limiting, unless specially so indicated. The invention is not otherwise limited, except for the recitation of the claims set forth below. All references cited herein are incorporated in their entirety.

What is claimed is:

1. A composition comprising:

a) a fluorescent polymer; and b) a compound comprising a recognition element which binds to a target biological agent and a property-altering element which increases or decreases the fluorescence emitted by the fluorescent polymer when complexed thereto, wherein the property-altering element and the recognition element are bound together by a tethering element, wherein, in the presence of binding between the recognition element and the target biological agent, the fluorescence emitted by the polymer differs from that emitted in the absence of binding between the recognition element and the target biological agent.

2. The composition of claim 1, wherein the recognition element is selected from the group consisting of chemical ligands, caffeine, theophylline, xanthine, hormones, antibodies, antibody fragments, oligonucleotides, antigens, polypeptides, glycolipids, proteins, protein fragments, enzymes, peptide nucleic acids and polysaccharides.

3. The composition of claim 1, wherein the property-altering element is selected from the group consisting of methyl viologen, quinones, metal complexes, fluorescent dyes and electron-accepting moieties electron donating moieties and energy transferring moieties.

4. The composition of claim 1, wherein the tethering element is selected from the group consisting of a single bond, a single divalent atom, a divalent chemical moiety up to 100 carbon atoms in length and a multivalent chemical moiety.

5. The composition of claim 1, further comprising an enhancement agent which makes the fluorescence of the polymer more easily detectable, wherein the enhancement agent is selected from the group consisting of energy transferring and energy donating moieties.

6. The composition of claim 1, wherein the fluorescent polymer comprises repeat units each containing a fluorescent dye pendant on a backbone moiety.

7. The composition of claim 1, wherein the fluorescent polymer comprises a fluorescent dye in a J-aggregate.

8. The composition of claim 6, wherein the fluorescent dye is selected from the group consisting of symmetrical cyanine dye chromophores, unsymmetrical cyanine chromophores, merocyanine dyes, positively charged dye chromophores, negatively charged dye chromophores and neutral dye chromophores.

9. The composition of claim 1, wherein the fluorescent polymer is affixed to a support.

10. The composition of claim 1, wherein the fluorescent polymer is bound to said property altering element by a second tethering element.

11. A kit for the detection of a target biological agent comprising:

a fluorescent polymer and a compound comprising a recognition element which binds to the target biological agent, a property-altering element which increases or decreases the fluorescence emitted by the fluorescent polymer when complexed thereto, and a tether connecting the recognition element and the property altering element.

12. The kit of claim 11, wherein the fluorescent polymer and the chemical moiety are contained in separate compartments with a separation therebetween, which may be removed by physical or chemical means.

13. A method of detecting a target biological agent in a sample comprising:

a) combining the fluorescent polymer and the compound of claim 1 with the sample;

b) permitting the recognition element to bind with target biological agent present in the sample; and c) determining the fluorescence emitted by the polymer in the presence of the sample;

wherein a difference in fluorescence emitted by the polymer in the presence of the sample compared with that emitted in the absence of the sample is indicative of the presence of said target biological agent.

14. The method of claim 13, wherein the amount of target biological agent present in the sample is correlated with the amount of the difference in fluorescence.

15. The method of claim 13, wherein the polymer is bound to the property altering element by a second tethering element.

16. The method of claim 13, wherein the sample is selected from the group consisting of liquid, vapor and aerosol.

17. The composition of claim 1, wherein the presence of the biological agent results in a complex between the compound and the biological agent, and wherein, when an electric field is applied, the complex is separated from the polymer and the fluorescence emitted by the polymer is increased or decreased from that emitted when separation does not occur.

18. The composition of claim 17, wherein the biological agent contains a positive or negative charge and the polymer has a charge opposite of the biological agent.

* * * * *